US 6,624,887 B1

(12) United States Patent
Kramer et al.

(10) Patent No.: US 6,624,887 B1
(45) Date of Patent: Sep. 23, 2003

(54) METHODS FOR DETERMINING THE PHYSIOLOGICAL STATE OF A PLANT

(75) Inventors: David M. Kramer, Pullman, WA (US); Colette Sacksteder, St Paul, MN (US)

(73) Assignee: Washington State University Research Foundation, Pullman, WA (US)

( * ) Notice: Subject to any disclaimer, the term of this patent is extended or adjusted under 35 U.S.C. 154(b) by 560 days.

(21) Appl. No.: 09/642,385

(22) Filed: Aug. 18, 2000

Related U.S. Application Data

(60) Provisional application No. 60/149,937, filed on Aug. 19, 1999.

(51) Int. Cl.[7] .............................. G01J 3/30; G01J 3/42; G01J 3/28
(52) U.S. Cl. ....................... 356/326; 356/318; 356/320; 356/322; 356/323
(58) Field of Search ................................ 356/318–327; 250/459.1, 458.1, 461.1

(56) References Cited

U.S. PATENT DOCUMENTS

| | | | | |
|---|---|---|---|---|
| 3,473,022 A | * | 10/1969 | Walz et al. | 422/82.09 |
| 4,533,252 A | * | 8/1985 | Cahen et al. | 356/432 |
| 4,650,336 A | | 3/1987 | Moll | 356/417 |
| 4,768,390 A | * | 9/1988 | Baker et al. | 73/865.6 |
| 5,029,245 A | | 7/1991 | Keranen et al. | |
| 5,426,306 A | * | 6/1995 | Kolber et al. | 250/458.1 |
| 5,519,219 A | | 5/1996 | Alexay et al. | |
| 5,854,063 A | * | 12/1998 | Li et al. | 435/287.1 |
| 5,981,958 A | * | 11/1999 | Li et al. | 250/459.1 |
| 6,005,722 A | | 12/1999 | Butterworth et al. | |
| 6,043,893 A | | 3/2000 | Treiman et al. | |
| 6,121,053 A | * | 9/2000 | Kolber et al. | 436/172 |

FOREIGN PATENT DOCUMENTS

| | | |
|---|---|---|
| DE | DD 248 433 A1 | 8/1987 |
| DE | 248 433 A-1 | 8/1987 |
| DE | DD 300 049 A7 | 5/1992 |
| DE | 300 049 A-7 | 5/1992 |

OTHER PUBLICATIONS

Kramer, D.M. et al., *Photosynthesis Research,* 56:103–112 (1998).
Joliet and Joliet, *Biochim. Biophys Acta.* 765:219–226 (1984).
Nishio and Whitmarsh, *Plant Physiol.,* 95:522–528 (1990).
Kramer and Crofts, *Biochim. Biophys Acta.,* 976:20–41 (1989).
Kramer, D.M. et al., "Control of photosynthesis and measurement of photosynthetic reactions in intact plants." In: N. Baker, (ed). Photosynthesis and the Environment. *Advances in Photosynthesis,* pp. 25–66. Dordrecht, The Netherlands: Kluwer Academic Press (1996).
Kramer, D.M. et al., *Photosynth. Res.,* 26:181–193 (1990).
Genty, B. et al., *Photosynth. Res.,* 25:249–257 (1990).
Sacksteder, C.A. et al., *Photosynthesis: Mechanisms and Effects.,* ed. Garab Kluwer Academic Publishers, Dordrect), 3:1621–1624 (1998).
Tanaka, K. et al., "Compound parabolic concentrator probe for efficient light collection in spectroscopy of biological tissue," *Applied Optics,* 35(4):758–636 (1996).

* cited by examiner

*Primary Examiner*—Russell Adams
*Assistant Examiner*—Magda Cruz
(74) *Attorney, Agent, or Firm*—Christensen O'Connor Johnson Kindness PLLC

(57) ABSTRACT

The present invention provides methods for measuring a photosynthetic parameter. The methods of the invention include the steps of: (a) illuminating a plant leaf until steady-state photosynthesis is achieved; (b) subjecting the illuminated plant leaf to a period of darkness; (c) using a kinetic spectrophotometer or kinetic spectrophotometer/fluorimeter to collect spectral data from the plant leaf treated in accordance with steps (a) and (b); and (d) determining a photosynthetic parameter from the spectral data. In another aspect, the invention provides methods for determining the physiological state of a plant.

44 Claims, 14 Drawing Sheets

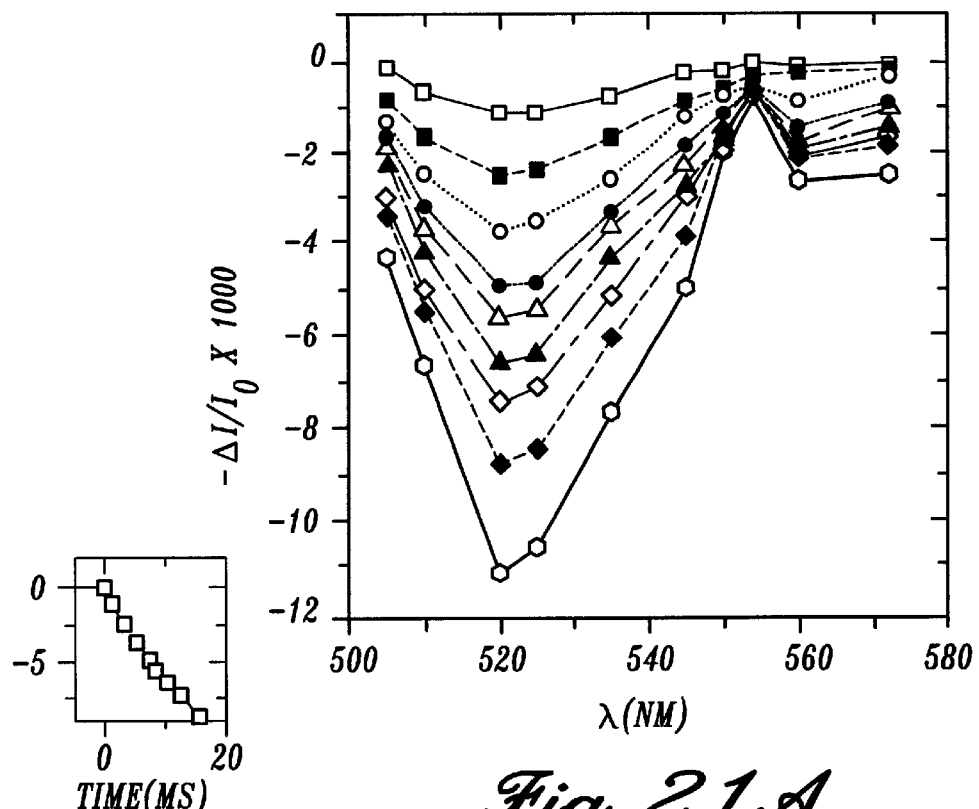
Fig. 21A.
Fig. 21B.
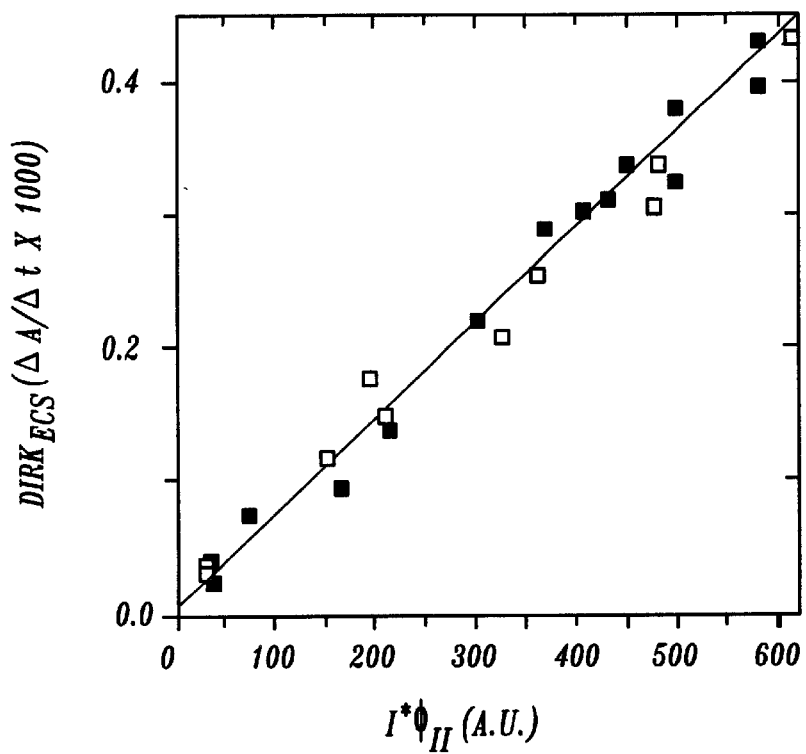
Fig. 22.

METHODS FOR DETERMINING THE PHYSIOLOGICAL STATE OF A PLANT

RELATED APPLICATIONS

The present application claims benefit of priority from U.S. Provisional Application No. 60/149,937, filed Aug. 19, 1999, under 35 U.S.C. §119.

GOVERNMENT RIGHTS

This invention was made with government support under Grant No. DE-FGO3-98ER20299 awarded by the United States Department of Energy. The government has certain rights in the invention.

FIELD OF THE INVENTION

The present invention relates generally to methods for measuring a photosynthetic parameter, and to methods for determining the physiological state of a plant.

BACKGROUND OF THE INVENTION

Photosynthesis in green plants takes place in two stages, the light reactions, which occur only when plants are illuminated, and the dark reactions, which can occur in the absence or presence of light. In the light reactions chlorophyll and other pigments of the photosynthetic cells absorb light energy and conserve it in chemical form as the two energy-rich products adenosine triphosphate (ATP) and nicotinamide adenine dinucleotide phosphate (NADPH); simultaneously, oxygen is evolved. In the dark reactions, the ATP and NADPH generated in the light reactions are used to reduce carbon dioxide to form glucose and other organic products.

In eukaryotic, photosynthetic cells, both the light and dark reactions take place in the chloroplast. Chloroplasts are surrounded by a continuous outer membrane. An inner membrane system encloses the internal compartment. Inside the latter, and often connected to the inner membrane, are many flattened, membrane-surrounded vesicles or sacs, called thylakoids, which are either single, or arranged in stacks called grana. The thylakoid membranes contain all the photosynthetic pigments of the chloroplast and most of the enzymes required for the primary light-dependent reactions. The fluid in the compartment surrounding the thylakoid vesicles, the stroma, contains most of the enzymes required for the dark reactions (i.e. $CO_2$ fixation).

Light energy is absorbed by photosynthetic pigments located within the thylakoid membranes. The primary light-absorbing pigment is chlorophyll. Photosynthetic cells of higher plants always contain two types of chlorophyll. One is always chlorophyll a, and the second in many species is chlorophyll b. In addition to chlorophylls, the thylakoid membranes contain secondary light-absorbing pigments, together called the accessory pigments, which include various carotenoids. The carotenoid pigments absorb light at wavelengths other than those absorbed by the chlorophylls and thus are supplementary light receptors.

The light-absorbing pigments of thylakoid membranes are arranged in functional sets or clusters called photosystems. The clusters can absorb light over the entire visible spectrum but especially well between 400 to 500 and 600 to 700 nanometers (nm). All the pigment molecules in a photosystem can absorb photons, but a special subset of the molecules, housed in complexes of proteins and cofactors, called the 'photochemical reaction centers' in each cluster ultimately convert the light energy into chemical energy. Other pigment molecules, that function to funnel light into the reaction centers, are housed in light-harvesting complexes. They function to absorb light energy, which they transmit at a very high rate to the reaction center.

There are two different kinds of photosystems: photosystem I (PS I), which is maximally excited by light at longer wavelengths, and has a high ratio of chlorophyll a to chlorophyll b; and photosystem II (PS II), which is maximally activated by light below 680 nm, and contains relatively more chlorophyll b and may also contain chlorophyll c. Photosystem I and Photosystem II are functionally linked by a chain of electron carriers, as shown in FIG. 1.

When light quanta are absorbed by photosystem I, energy-rich electrons are expelled from the reaction center and flow down a chain of electron carriers to $NADP^+$ to reduce it to NADPH. This process leaves a deficit of electrons (an electron hole) in photosystem I. This hole is, in turn, filled by an electron expelled by illumination of photosystem II, which arrives via a connecting chain of electron carriers, including a pool of about 6 plastoquinone molecules per reaction center, the cytochrome $b_6f$ complex and plastocyanin. The resulting electron hole in photosystem II is filled by electrons extracted from water. This pattern of electron flow is usually referred to as the "Z-scheme". Additionally, absorbed light can be reemitted in the form of fluorescence.

The thylakoid membrane has an asymmetric molecular organization. The electron-transferring molecules in the connecting chain between photosystem II and photosystem I are oriented in the thylakoid membrane in such a way that electron flow results in the net movement of $H^+$ ions across the membrane, from the outside of the thylakoid membrane to the inner compartment. Thus photoinduced electron flow generates an electrochemical gradient of $H^+$ ions across the thylakoid membrane, so that: 1) the inside of the thylakoid vesicles becomes more acid than the outside, storing energy as a difference in pH (known as $\Delta pH$); and 2) the inside of the thylakoid membrane becomes more positively charged than the outside, storing energy as an electrical field (known as $\Delta\Psi$). The sum of energies stored as $\Delta pH$ and $\Delta\Psi$ drives the synthesis of ATP from ADP and inorganic phosphase, for later use in plant biochemical processes.

Lumen acidification also initiates processes that down-regulate the entire photosynthetic apparatus. The down-regulatory processes reduce the amount of light transferred from the light harvesting pigments to the photosystem II reaction centers, thus protecting the reaction centers from over-exposure to light.

Another type of light-induced electron flow that can take place in chloroplasts is called cyclic electron flow, to differentiate it from the normally unidirectional or noncyclic electron flow of the "Z-scheme" that proceeds from $H_2O$ to $NADP^+$. As shown in FIG. 2, cyclic electron flow involves only photosystem I. It is called cyclic because the electron boosted to the first electron acceptor in photosystem I (an iron-sulfur cluster) by illumination of photosystem I, instead of passing to $NADP^+$, flows back into the electron hole of photosystem I by a shunt or bypass pathway. As shown in FIG. 2, this shunt involves some of the electron carriers of the chain between photosystems I and II, including the pool of plastoquinone molecules, the cytochrome $b_6f$ complex and plastocyanin. Thus, illumination of photosystem I can cause electrons to cycle continuously out of the reaction center of photosystem I and back into it. During cyclic electron flow there is no net formation of NADPH, nor is there any oxygen evolution. However, cyclic electron flow is accompanied by proton pumping into the lumen (inside)

of the thylakoid vesicle. Thus cyclic electron flow can generate ATP, and this process is referred to as cyclic photophosphorylation. Cyclic electron flow is thought to have two functions: to supply ATP when amply supplied with reducing power in the form of NADPH, and to initiate down-regulation by acification of the thylakoid lumen.

The methods of the invention allow one or more photosynthetic parameters of a plant to be determined by measuring the steady-state turnover rates and resistances to turnover of several photosynthetic reactions and protein complexes just after a rapid light-to-dark transition. The relaxation processes that occur just after switching off the light reflect the processes that occurred in the light, and thus the measurements provide information of the steady-state of photosynthesis. The physiological state of a plant (such as whether the plant is subject to an environmental stress) affects photosynthesis. Thus, the methods of the invention can be used to measure one or more photosynthetic parameters which, in turn, can be used to indicate the presence of one or more plant stresses before they become apparent as lowered crop yields or other visible symptoms.

SUMMARY OF THE INVENTION

The present invention provides methods for measuring a photosynthetic parameter. The methods of the invention include the steps of: (a) illuminating a plant leaf until steady-state photosynthesis is achieved; (b) subjecting the illuminated plant leaf to a period of darkness; (c) using a kinetic spectrophotometer or kinetic spectrophotometer/fluorimeter to collect spectral data from the plant leaf treated in accordance with steps (a) and (b); and (d) determining a photosynthetic parameter from the spectral data. In the practice of the present invention, the plant leaf can be attached or detached from its parent plant.

Typically, the illuminated plant is subjected to darkness for a period of from 2 milliseconds to 120 seconds, depending on the photosynthetic process that is being measured. It will be understood that the plant subjected to darkness is nonetheless illuminated (for at least a portion of the dark period) by one or more measuring beams of light generated by the kinetic spectrophotometer or kinetic spectrophotometer/fluorimeter. Depending upon the wavelength(s) of the measuring beam(s), many processes can be measured by their absorbance of light, which can be expressed as the differences in transmission normalized to a standard transmission ($\Delta I/I_0$). Wavelength of light is measured in units of nanometers (nm).

Representative examples of photosynthetic parameters that can be determined using the methods of the invention are: one or more redox reactions of the photosystem I primary electron donor (the required spectral data can be obtained, for example, by illuminating the plant leaf with a measuring beam of light having a wavelength of 703 nm, or a wavelength in the range of 800–850 nm); one or more redox reactions of plastocyanin (the required spectral data can be obtained, for example, by illuminating the plant leaf with a measuring beam of light having a wavelength of 600 nm, or a wavelength in the range of 850–925 nm); one or more redox reactions of cytochrome f (the required spectral data can be obtained, for example, by illuminating the plant leaf with a measuring beam of light having a wavelength selected from the group consisting of 435, 545, 554 and 560 nm); one or more redox reactions of cytochrome b (the required spectral data can be obtained, for example, by illuminating the plant leaf with a measuring beam of light having a wavelength selected from the group consisting of 420, 563 and 572 nm); one or more redox reactions of the primary quinone acceptor of photosystem II (the required spectral data can be obtained, for example, by illuminating the plant leaf with a measuring beam of light having a wavelength of 300 nm, or a wavelength selected from the group consisting of 545, 550 and 555 nm (which measures the Stark-shift of the nearby pheophytin)); the conversion of violaxanthin to antheraxanthin and zeaxanthin (in response to thylakoid lumen acidification) in the light harvesting complexes (the required spectral data can be obtained, for example, by illuminating the plant leaf with a measuring beam of light having a wavelength of 505 nm); the amount of energy stored across the thylakoid membrane (the required spectral data can be obtained, for example, by illuminating the plant leaf with a measuring beam of light having a wavelength selected from the group consisting of 470 and 520 nm); and the fraction of open photosystem II reaction centers (the required spectral data can be obtained, for example, by illuminating the plant leaf with a measuring beam of light having a wavelength greater than 650 nm).

Additional examples of photosynthetic parameters that can be determined from the spectral data obtained from plant leaves treated in accordance with the methods of the invention include: electron ($e^-$) transfer through photosystem I; electron ($e^-$) transfer through photosystem II; the quantum efficiency of the photosystem I and II antennae complexes; proton transfer across the thylakoid membrane; the percentage of electron transfer going through the cyclic pathway; the percentage of electron transfer going through the linear pathway (the so-called Z-scheme); the amplitude of the electrochromic shift (which is an indication of the amount of energy stored across the thylakoid membrane as proton motive force); and the chlorophyll content.

Spectral data is collected using a kinetic spectrophotometer or kinetic spectrophotometer/fluorimeter. One example of a kinetic spectrophotometer is a diffused-optics flash kinetic spectrophotometer (DOFS), which is specifically designed to measure absorbance and fluorescence changes in leaves and to decrease interference from light scattering changes. A preferred kinetic spectrophotometer useful in the practice of the invention generates a measuring light beam having a direction that is randomized before and after passing through the plant leaf.

The determined photosynthetic parameter(s) can be used to provide information about the type and amount of photosynthetic activity in a plant leaf, or in a whole plant, or population of plants. Additionally, the determined photosynthetic parameter(s) can be used to ascertain whether the subject plant is experiencing one or more of a variety of environmental and/or physiological stresses, such as temperature stress, drought stress and nutrient stress (including nitrogen stress). Thus, in one aspect, the present invention provides methods for determining the physiological state of a plant comprising: (a) illuminating a plant leaf until steady-state photosynthesis is achieved; (b) subjecting the illuminated plant leaf to a period of darkness; (c) using a kinetic spectrophotometer or kinetic spectrophotometer/fluorimeter to collect spectral data from the plant leaf treated in accordance with steps (a) and (b); (d) determining a value for a photosynthetic parameter from the spectral data; and (e) using the determined value for the photosynthetic parameter to determine the physiological state of the plant.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 21A shows spectral and kinetic changes that occur upon rapid shuttering of actinic light. Changes in absorbance, estimated by $-\Delta I/I_0$, were obtained in an intact tobacco plant leaf using a diffused optics flash spectrophotometer at a series of wavelengths as described in Example 10. The background actinic light was set at 900 $\mu$moles photons m$^{-2}$s$^{-1}$ and shuttered for approximately 40 ms every 15 s. Data was averaged over 8 traces at each wavelength. Measurements were made at 1.4, 3.4, 5.4, 7.4, 8.4, 10.4, 12.4, 15.4 and 25.4 ms after half shutter closure for curves represented by open squares, closed squares, open circles, closed circles, open triangles, closed triangles, open diamonds, closed diamonds and open hexagons, respectively. FIG. 21B shows dark interval relaxation kinetics at 520 nm measured under the conditions described in the description of FIG. 21A. Shutter was half closed at time zero.

FIG. 22 shows a comparison of DIRK$_{ECS}$, estimating proton pumping, and $i^*\phi_{II}$, estimating electron flux through PS II. Values were calculated as described in Example 10. The open and closed symbols represent data taken from two separate plants. The r-value of the best-fit line was 0.995.

DETAILED DESCRIPTION OF THE PREFERRED EMBODIMENT

Figure 1:
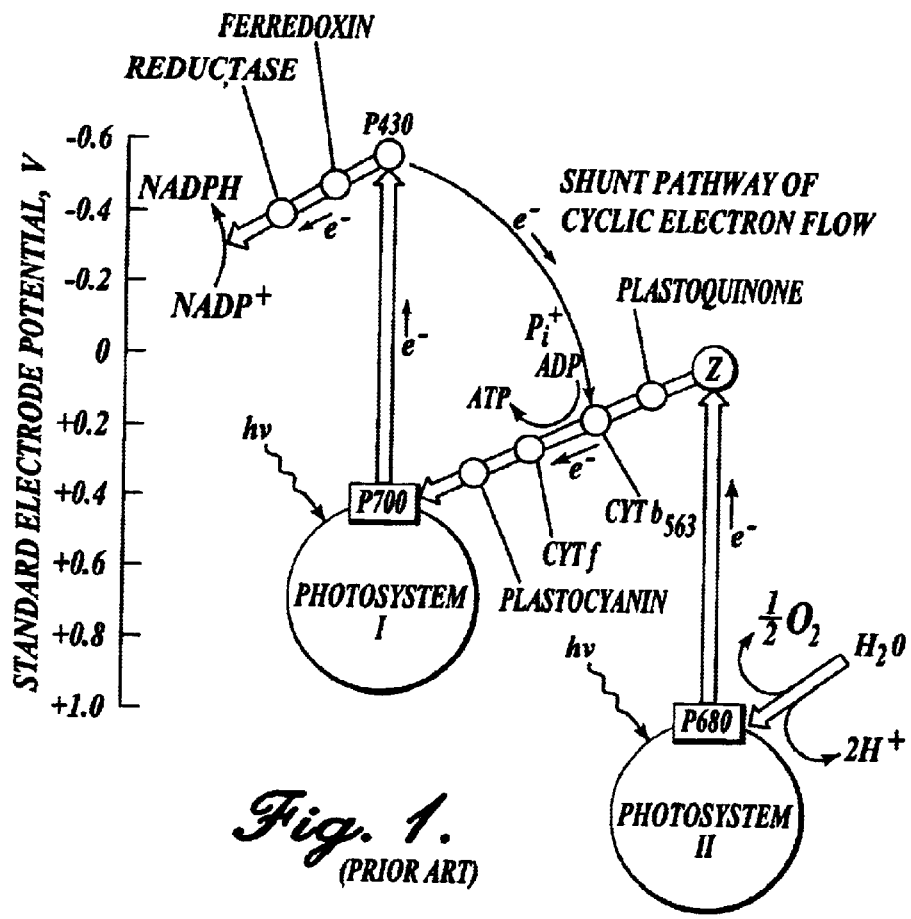
FIG. 1 shows the Z-scheme of electron transfer in the light reaction of photosynthesis.
Figure 2:
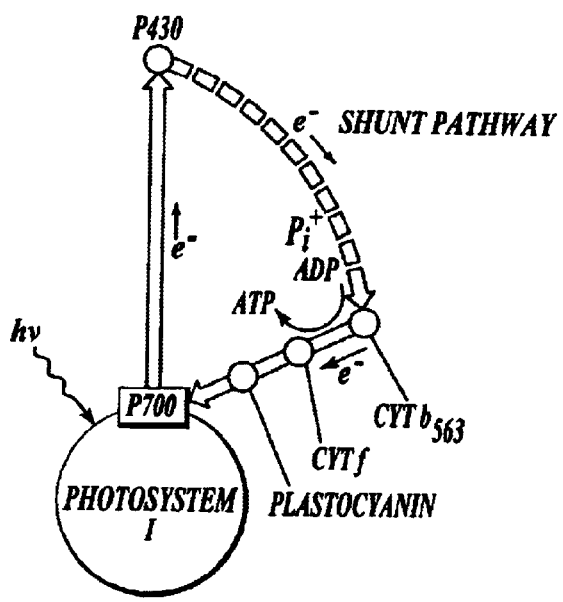
FIG. 2 shows cyclic electron flow in the light reaction of photosynthesis.

As used herein, the term "steady-state photosynthesis" means that the concentrations of photosynthetic intermediates in the light reactions of photosynthesis are not changing significantly over the time scale of the period during which one or more photosynthetic parameters are being measured using the methods of the present invention. For example, if the concentrations of photosynthetic intermediates in the light reactions of photosynthesis do not change significantly over the time scale of one second, this state would be considered "steady-state photosynthesis" in the context of using the methods of the invention to measure electron transfer during a time period of 10 milliseconds.

As used herein, the term "kinetic spectrophotometer" refers to an instrument capable of measuring changes in the light absorbance of a material (such as a plant leaf) over time.

As used herein, the term "kinetic spectrophotometer/fluorimeter" refers to an instrument capable of measuring changes in the light absorbance and/or changes in the fluorescent radiation emission of a material (such as a plant leaf) over time.

As used herein the term "photosynthetic parameter" refers to any photosynthetic reaction that can be quantitatively measured using a kinetic spectrophotometer and/or kinetic spectrophotometer/fluorimeter. Representative examples of photosynthetic parameters include: light-driven fluxes of protons through photosystems I and II, the levels of light-driven ATP synthesis, the control of light capture by the antenna complexes, the storage of proton motive force across the thylakoid membrane (both as an electric field and as a difference in pH values), the redox states of the electron transfer components in the light and dark.

Many redox reactions in photosynthesis can be measured using the methods of the invention, including the redox reactions of the photosystem I primary electron donor ($P_{700}$, measured at 703 nm, and in the near infrared at about 800–850 nm), plastocyanin (at about 600 nm, or in the near infrared at about 850–925 nm), cytochrome f (at 435, 545, 554 and 560 nm), cytochrome b (at 420, 563 and 572 nm), the primary quinone acceptor of photosystem II (known as $Q_A$ in the UV at about 300 nm or via the Stark-shift of the nearby pheophytin at 545, 550 and 555 nm). The downregulatory process of conversion of violaxanthin to antheraxanthin and zeaxanthin in the light harvesting complexes (in response to lumen acidification) can be measured at 505 nm. Two major signals indicate the energization of the thylakoid membrane. The energy stored as $\Delta\Psi$ can be measured as a shifting of the absorbance spectrum of carotenoids in the light harvesting complexes, resulting in signals at about 520 and 470 nm. The $\Delta pH$ component of thylakoid energy induces changes in the shape of the thylakoid vesicles, causing changes in the scattering of light. In an absorbance spectrophotometer, changes in light scattering appear as absorbance changes, having a broad spectrum with peak at about 535 nm.

In addition to absorbance, changes in the chlorophyll fluorescence of plants, measured at wavelengths greater than 650 nm, can yield important information about the state of the photosynthetic apparatus. Photons of light absorbed by pigments in the light harvesting complexes are called excitons. Excitons can decay by several pathways, the most prominent being photochemistry in the reaction centers, fluorescence, non-radiative decay (to heat) and the formation of triplet states (intersystem crossing). The rates of exciton decay down these pathways are modulated by the state of the chloroplast. When the photosystem II reaction centers are active (i.e. in 'open' states) most excitons are delivered to them, and used for performing photochemistry. When the photosystem II centers are closed, excitons decay by other routes, such as fluorescence. The increased flux of excitons through the fluorescence decay pathway is then an indicator that photosystem II reaction centers are in inactive states. During normal photosynthesis, photosystem II reaction centers are excited by light, and pass through several inactive, highly fluorescent states before returning to open states that can accept more light energy. When the input of light energy is high, the input of excitons into the reaction centers competes with the return to open states and the fraction of photosystem II centers in closed states increases, increasing the fraction of excitons that decay through fluorescence. By analyzing fluorescence yield, the fraction of open photosystem II reaction centers can be estimated. In addition, the rate of photosystem II center reopening can be observed by measuring the kinetics of decay of highly fluorescent states after light exposure.

The major processes that downregulate photosynthesis decrease the fraction of excitons that reach the reaction centers. This is accomplished by "shunting" excitons to heat, via non-radiative processes, and thus these processes are collectively termed non-photochemical quenching (NPQ) of excitation energy. The activation of NPQ affects fluorescence because the quenching process also competes with the decay of excitons to fluorescence. Thus, the maximal fluorescence when all reaction centers are closed, decreases when downregulation is activated.

Other representative examples of photosynthetic parameters that can be measured using the methods of the present invention include: cyclic electron transfer around photosystem I and photosystem II (see, e.g., Example 2 herein); light driven proton flux (see, e.g., Example 3 herein); resistance to turnover of photosynthetic complexes (see, e.g., Example 4 herein); measurement of the efficiency of light capture by photosystem II (see, e.g., Example 5 herein); and ATP synthase activity and $P_{700}$ reduction (see, e.g., Example 6 herein).

In the practice of the present invention, spectral data is collected using a kinetic spectrophotometer or kinetic spectrophotometer/fluorimeter. One example of a kinetic spectrophotometer is a diffused-optics flash kinetic spectrophotometer (DOFS). The kinetic spectrophotometers and kinetic spectrophotometer/fluorimeters useful in the practice of the present invention preferably resolve spectral changes that occur in one millisecond or faster. In addition, the kinetic spectrophotometers and kinetic spectrophotometer/fluorimeters useful in the practice of the present invention preferably distinguish, either spectrally or kinetically, absorbance changes from light-scattering changes. The DOFS instrument does this by using diffused measuring light.

Figure 3:
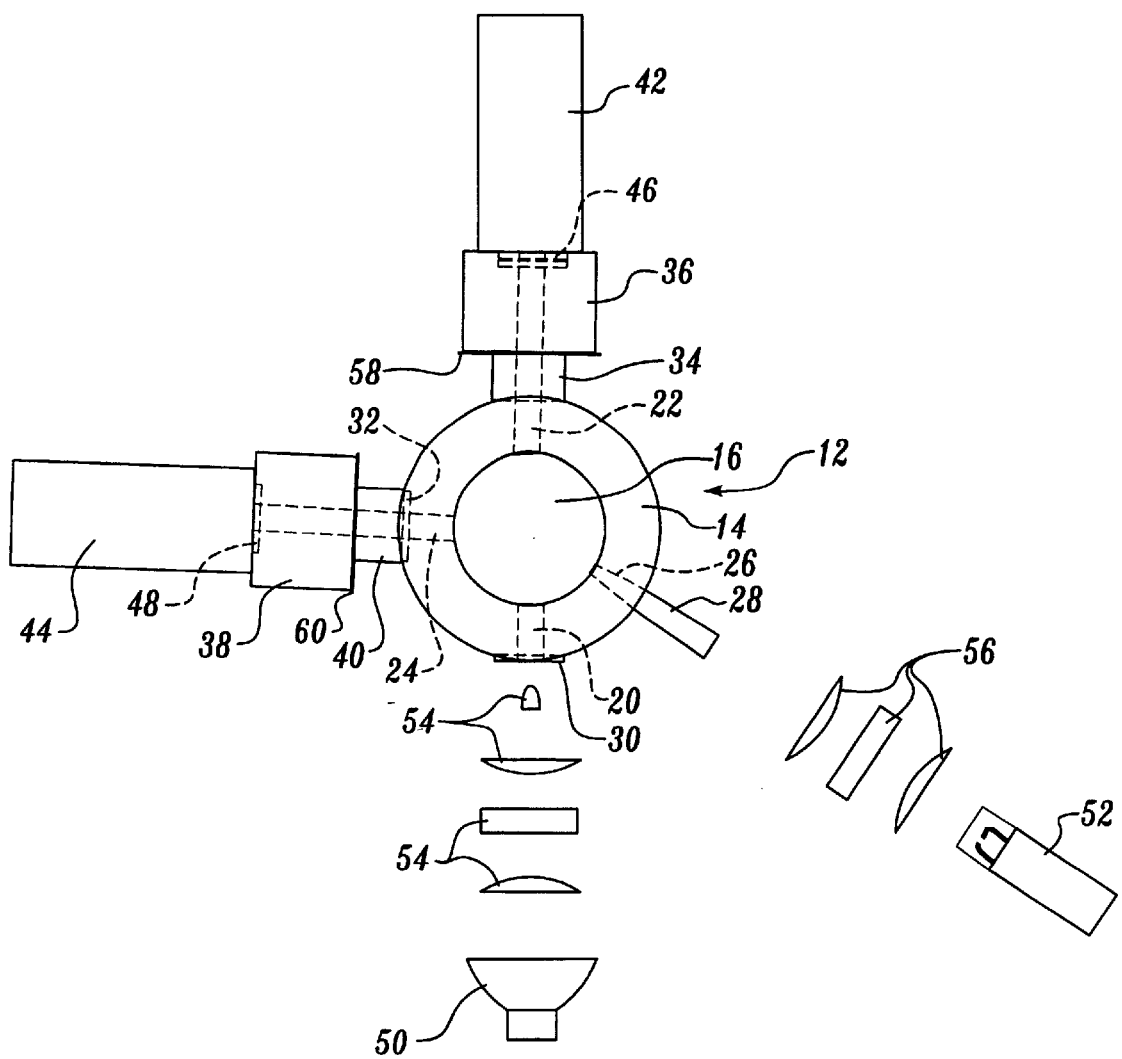
FIG. 3 shows an exploded schematic view of a diffused-optics flash kinetic spectrophotometer.

FIG. 3 shows a representative example of a diffused optics flash spectrophotometer 10 useful in the practice of the present invention. Spectrophotometer 10 includes primary scrambling chamber 12. As shown more clearly in FIG. 4, primary scrambling chamber 12 includes a generally cylindrical body 14, defining a lumen 16, and a detachable cap 18. Primary scrambling chamber body 14 can be made from any suitable, reflective and light-scattering material, such as Spectralon plastic (manufactured by Labsphere, North Sutton, N.H.). Primary scrambling chamber body 14 also defines an actinic light entrance port 20, a sample exit port 22, a reference exit port 24 and a probe entrance port 26 which receives a compound parabolic concentrator 28.

Actinic light entrance port 20 is located directly opposite sample exit port 22. The entrance to actinic light entrance port 20 is covered by a dichroic blocking filter 30, such as a 6400 LP Omega Optical filter (shown in FIG. 3). Reference exit port 24 is covered by a color blocking filter 32 (also shown in FIG. 3). In one embodiment, primary scrambling chamber 12 has an outside diameter of approximately 9.0 cm, an inside diameter of approximately 4.0 cm, and an inside height of approximately 5.5 cm.

Referring again to FIG. 3, primary scrambling chamber 12 is connected, by a sample connecting portion 34, to a sample secondary scrambling chamber 36, and to a reference secondary scrambling chamber 38 by a reference connecting portion 40. Sample secondary scrambling chamber 36 is connected to a sample detector 42, and reference secondary scrambling chamber 38 is connected to reference detector 44. A sample blocking filter 46 is positioned between sample secondary scrambling chamber 36 and sample detector 42. Similarly, a reference blocking filter 48 is positioned between reference secondary scrambling chamber 38 and reference detector 44.

Diffused optics flash spectrophotometer 10 also includes an actinic light source 50, a measuring light source 52, an actinic light lens system 54, and a measuring light lens system 56. A sample 58 for analysis is placed between sample connecting portion 34 and sample secondary scrambling chamber 36. A reference sample 60 is placed between reference connecting portion 40 and reference secondary scrambling chamber 38. Diffused optics flash spectrophotometer 10 is described in Kramer, D. M. and Sacksteder, C. A., *Photosynthesis Research* 56: 103–112 (1998), which publication is incorporated herein by reference.

Figure 4:
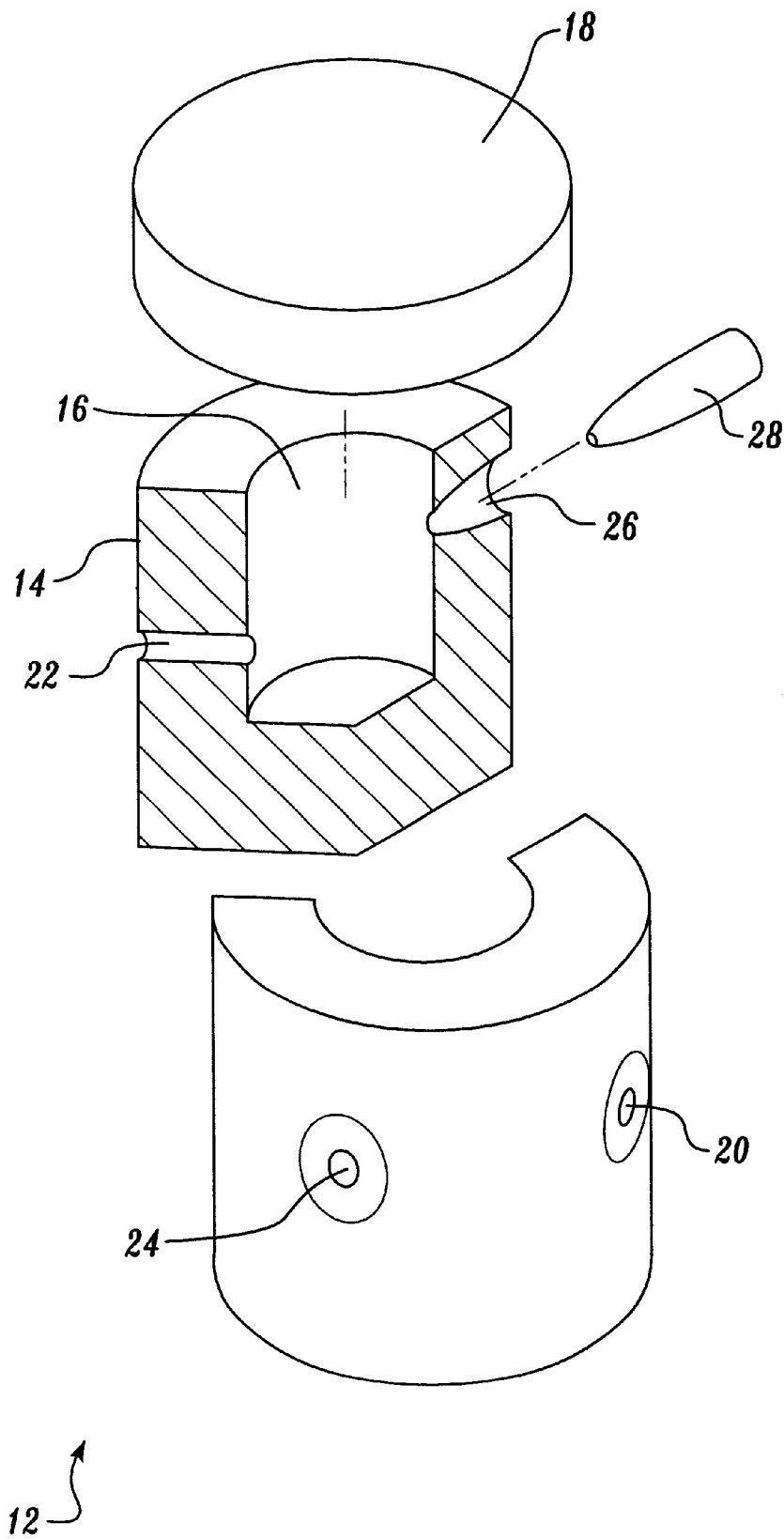
FIG. 4 shows an exploded perspective view, partially in cross-section, of a primary scrambling chamber of the diffused-optics flash kinetic spectrophotometer of FIG. 3.

A feature of diffused optics flash spectrophotometer 10 shown in FIGS. 3 and 4 is that interference from light-scattering changes is minimized by randomizing the direction of the measuring beam both before and after passing through sample 58 (such as a plant leaf). To this end, diffused optics flash spectrophotometer 10 includes primary scrambling chamber 12, sample secondary scrambling chamber 36, and reference secondary scrambling chamber 38 that are each constructed from a highly reflective and light-scattering plastic. Samples are placed between primary scrambling chamber 12 and sample secondary scrambling chamber 36, and between primary scrambling chamber 12 and reference secondary scrambling chamber 38, so that light reaching sample detector 42 and reference detector 44 has been diffused both before and after passing through sample 58, and reference sample 60, respectively.

Thus, in operation actinic light source 50 generates actinic light which passes through actinic light lens system 54 and enters primary scrambling chamber 12 through actinic light entrance port 20. Scattered actinic light is prevented from striking reference sample 60 by color blocking filter 32. Examples of actinic light sources 50 include a red light emitting diode (e.g., LED, HLMP-8103, Hewlett Packard), or a heat-filtered, 100 W tungsten-halogen lamp, or a xenon lamp, or a laser.

Measuring light source 52 generates a measuring light flash which passes through measuring light lens system 56 that includes a 25 mm focal length lens and a 2–3 nm narrow bandpass interference filter. The measuring light flash is then filtered through compound parabolic concentrator 28 that both concentrates and diffuses the measuring light flash which then enters primary scrambling chamber 12. Primary scrambling chamber 12 divides the measuring light flash equally between sample exit port 22 and reference exit port 24. Measuring light is prevented from escaping from actinic light port 20 by dichroic blocking filter 30 (e.g., 6400 LP Omega Optical) which reflects blue and green light back into primary scrambling chamber 12 while allowing red or near IR actinic light to pass. Spectral data is collected by shuttering actinic light impinging on sample 58, thereby subjecting sample 58 to a period of darkness. During the dark period, measuring light source 52 generates a flash of measuring light of one or more desired wavelength(s) which impinges on sample 58 and yields measurable spectral data.

Data collected using the methods of the present invention show the relaxation of absorbance changes upon briefly shuttering actinic light impinging on a sample (such as a plant leaf). The initial changes reflect what occurred just prior to shutter closure. It is difficult to measure fluxes through a process in the steady-state because the concentrations of reaction intermediates (i.e., what is being measured) do not change. The steady-state must be disturbed to measure it. The inventive techniques do this in a non-invasive way, by inhibiting only the light-driven reactions, and following the progress (or relaxation) of the non-light driven reactions, in plant photosynthesis.

Figure 5:
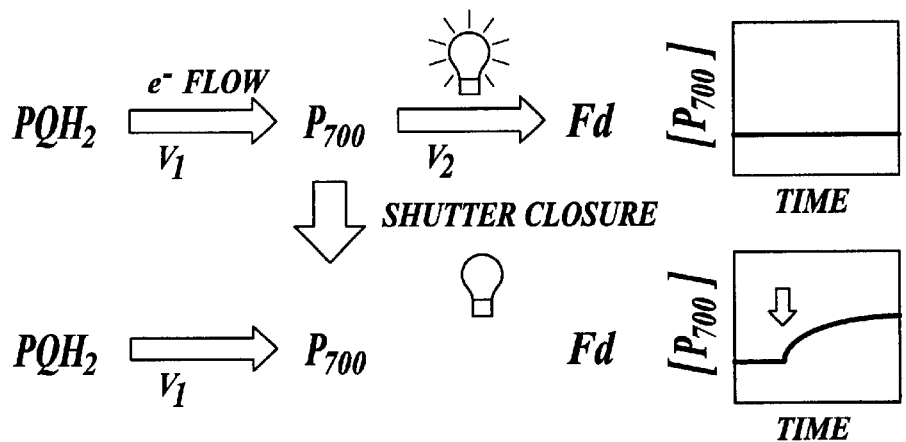
FIG. 5 shows a schematic diagram of the methods of the present invention as applied to the measurement of the steady-state turnover of PS I ($P_{700}$).

By way of example, FIG. 5, shows how the methods of the invention can be used to measure the steady-state turnover of PS I ($P_{700}$). In the steady-state, the rate of light-driven oxidation of $P_{700}$ ($v_2$) is precisely counterbalanced by the rate of its rereduction via turnover of the cytochrome $b_6f$ complex ($v_1$), leading to a stable $P_{700}$ redox state. By briefly and rapidly shuttering the light, $v^2$ is temporarily inhibited, thus allowing the system to relax. The initial changes in the concentration of reduced $P_{700}$ (the dark relaxation) reflect $v_1$, and are proportional to the flux through the system just prior to the shuttering. It should be noted that the methods of the present invention are not sensitive to changes in the PS I acceptor side redox state (see, Klughammer C and Schreiber U *Planta* 192: 261–268 (1994)) when used to measure PS I flux, and so should be free from this potential artifact.

The measured photosynthetic parameter(s) can be used to determine whether the subject plant is experiencing one or more of a variety of environmental and/or physiological stresses, such as temperature stress, drought stress and nutrient stress (including nitrogen stress). Thus, in one aspect, the present invention provides methods for determining the physiological state of a plant comprising: (a) illuminating a plant leaf until steady-state photosynthesis is achieved; (b) subjecting the illuminated plant leaf to a period of darkness; (c) using a kinetic spectrophotometer or kinetic spectrophotometer/fluorimeter to collect spectral data from the plant leaf treated in accordance with steps (a) and (b); (d) determining a value for a photosynthetic parameter from the spectral data; and (e) using the determined value for the photosynthetic parameter to determine the physiological state of the plant. In one embodiment, the step of using the determined value for the photosynthetic parameter to determine the physiological state of a plant comprises the step of comparing the determined value for the photosynthetic parameter to a reference value for the same photosynthetic parameter determined from spectral data obtained from one or more reference plants. Typically a difference is observed between the determined value for the photosynthetic parameter and the reference value for the photosynthetic parameter. The difference can typically be correlated with the presence of a physiological stress in the plant.

For example, utilizing the foregoing methods for determining the physiological state of a plant, changes in the following, representative, photosynthetic parameters can be correlated with the presence of a physiological stress in a plant: an increase in ATP synthase activity (relative to ATP synthase activity in one or more reference plants) is correlated with the presence of drought stress in the plant; an increase in $P_{700}$ reduction (relative to $P_{700}$ reduction in one or more reference plants) is correlated with the presence of drought stress in the plant; an increase in the proton/electron resistance ratio (relative to the proton/electron resistance ratio in one or more reference plants) is correlated with the presence of drought stress in the plant; a decrease in ATP synthase activity (relative to ATP synthase activity in one or more reference plants) is correlated with the presence of nitrogen stress in the plant; a decrease in $P_{700}$ reduction (relative to $P_{700}$ reduction in one or more reference plants) is correlated with the presence of nitrogen stress in the plant; a decrease in the proton/electron resistance ratio (relative to the proton/electron resistance ratio in one or more reference plants) is correlated with the presence of nitrogen stress in the plant.

The following examples merely illustrate the best mode now contemplated for practicing the invention, but should not be construed to limit the invention.

EXAMPLE 1

Figure 6:
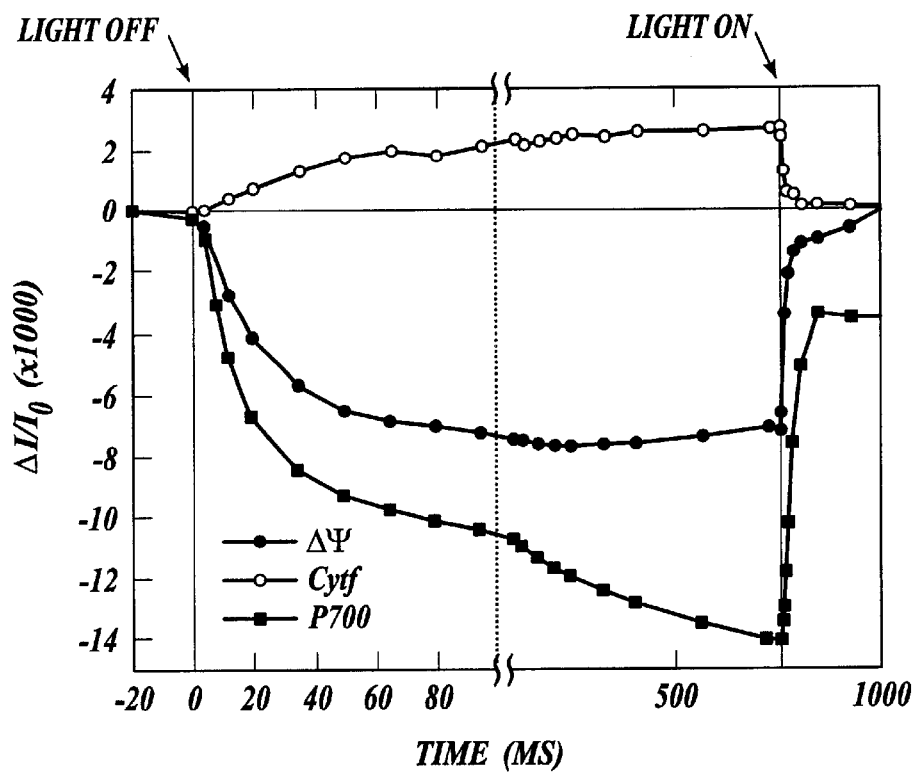
FIG. 6 shows data collected from an intact Poinsettia leaf using a diffused-optics flash kinetic spectrophotometer to measure the relaxation kinetics of cytochrome f and $P_{700}$, and the electrochromic shift ($\Delta\Psi$) during a brief shuttering of continuous illumination (300 $\mu$mole photons/m$^2$/s).

Relaxation Kinetics of Cytochrome f, $P_{700}$, and the Electrochromic Shift in an Intact Poinsettia Leaf FIG. 6 shows data collected from an intact Poinsettia leaf using diffused-optics flash kinetic spectrophotometer 10 to measure the relaxation kinetics of cytochrome f and $P_{700}$, and the electrochromic shift ($\Delta\Psi$) during a brief shuttering of continuous illumination (300 μmole photons/m²/s).

Leaves on intact plants were placed in diffused-optics flash kinetic spectrophotometer 10 and illuminated with continuous, actinic light. The light was shuttered either with a mechanical shutter or by switching off a bank of light-emitting diodes.

Cytochrome f redox changes were deconvoluted from the electrochromic shift and other species by four different methods: 1) based on that reported by Joliot and Joliot (Biochim. Biophys Acta. 765: 219–226 (1984)), a straight baseline, between the 545 nm and 573 nm absorbance changes, was subtracted from the 544 nm changes, i.e. $\Delta I/I_{cyt\,f}=(\Delta I/I_{554}-\Delta I/I_{545})-0.32(\Delta I/I_{573}-\Delta I/I_{545})$; 2) the technique of Nishio and Whitmarsh (Plant Physiol. 95: 522–528 (1990), i.e. $\Delta I/I_{cyt\,f}=(\Delta I/I_{554}-\Delta I/I_{560})$; 3) the technique of Kramer and Crofts (Biochim Biophys Acta 976: 20–41 (1989)) where a fraction (10–13%) of the 515 nm change is subtracted from the difference between the absorbance at 545 nm and 554 nm; and 4) assuming 545 nm to be nearly isobestic for cytochrome f redox changes and all absorbance changes at this wavelength were to be caused by the electrochromic shift, the electrochromic shift spectrum published by Witt was scaled to the 545 nm absorbance changes and subtracted from the entire spectrum. Though the different techniques yielded different signal extents, which most likely depended upon the differences in the extinction coefficients and the wavelengths employed in each, they all yielded similar kinetics when their amplitudes were normalized. Results using the technique of Joliot and Joliot are reported herein, mainly because the data could be directly compared to a large body of previously accumulated data.

Figure 7:
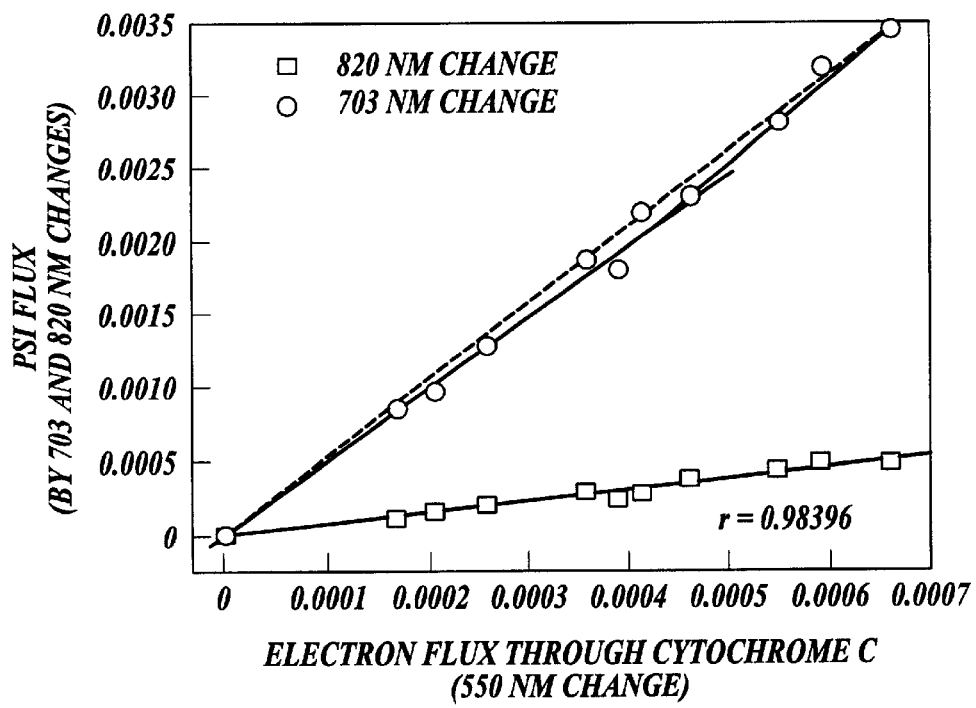
FIG. 7 shows the linear relationship between $O_2$ evolution and dark-interval relaxation kinetic analysis.

The results presented in FIG. 6 show that rates of linear electron flow can be readily measured with the methods of the present invention by monitoring electron transfer through PS I or cytochrome f. As expected, a linear relationship was observed between estimates of electron transfer rates (shown as PS1 flux) obtained by measurement of $O_2$ evolution (in a leaf disk electrode) and analysis of the 820 nm change (in this case measured by reflectance spectroscopy) in a tobacco leaf disk (See FIG. 7). $O_2$ evolution was measured using a Clark electrode using the methods disclosed in Sacksteder and Kramer (1998), supra. An $O_2$ concentration of 2% was used to minimize photorespiration.

EXAMPLE 2

Measurement of Cyclic Electron Transfer Around Photosystem I and Photosystem II

Figure 8:
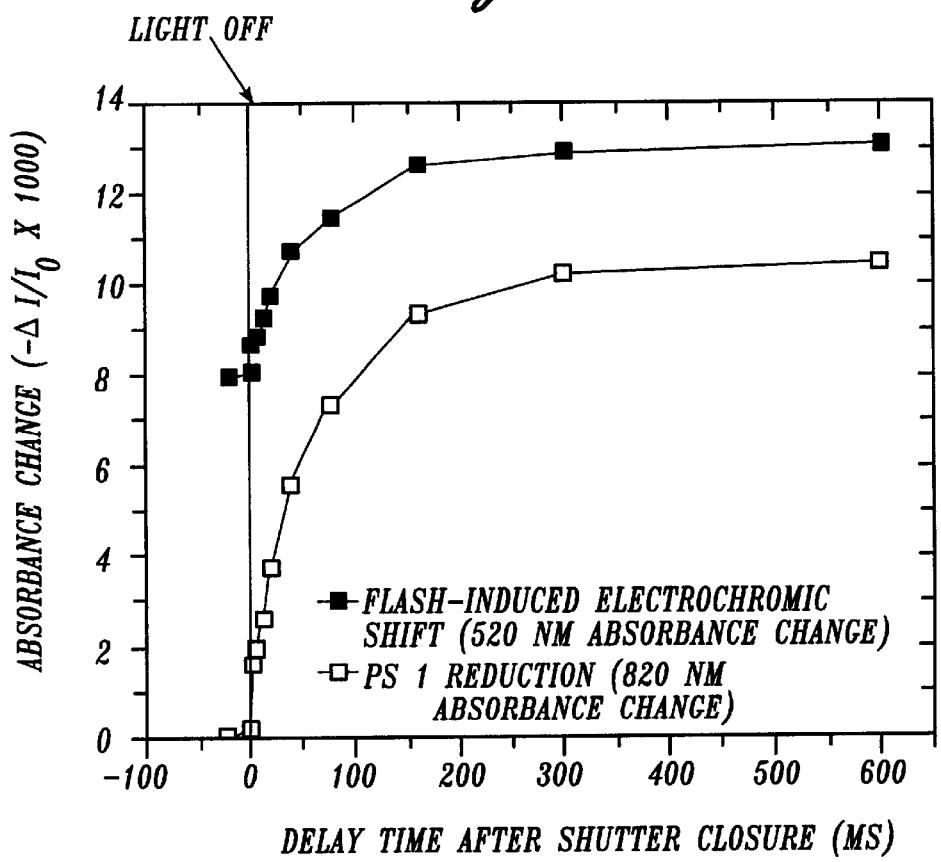
FIG. 8 shows plots of electrochromic shift measured at a measuring beam wavelength of 520 nm, and PS I reduction measured at a measuring beam wavelength of 820 nm, versus delay time after shutter closure, as described in Example 2.

The methods of the present invention can also be used to measure cyclic electron transfer around both photosystems as long as a measurement of the fraction of open photosystems can be made. For example, the number of open PS I and PS II centers was probed by exciting the leaf with saturating laser pulses and monitoring the extent of the rapid rise of the electrochromic shift (i.e., $\Delta A$ at about 520 nm). The experiment was repeated with the laser flash given at a range of times after shutter closure. Plots of the extent of laser-induced electrochromic shift, proportional to the fraction of open centers against the delay time between shutter closure and laser flash, (FIG. 8) represent the kinetics of center reopening (in a tobacco leaf under continuous 300 μmol photons m$^{-2}$s$^{-1}$ red light), the initial rate of which is proportional to the steady-state turnover rate of both PS I and PS II centers. The absorbance changes that occurred at around 820 nm, upon shutter closure, indicating the reopening of photosystem I centers as $P_{700}$ was reduced, was also monitored (FIG. 8). As is clear from FIG. 8, in healthy intact leaves, the initial rates of PS I and PS II reopening are nearly equal, as expected for linear electron transfer.

EXAMPLE 3

Measurement of Light-Driven Fluxes of Protons

Figure 9:
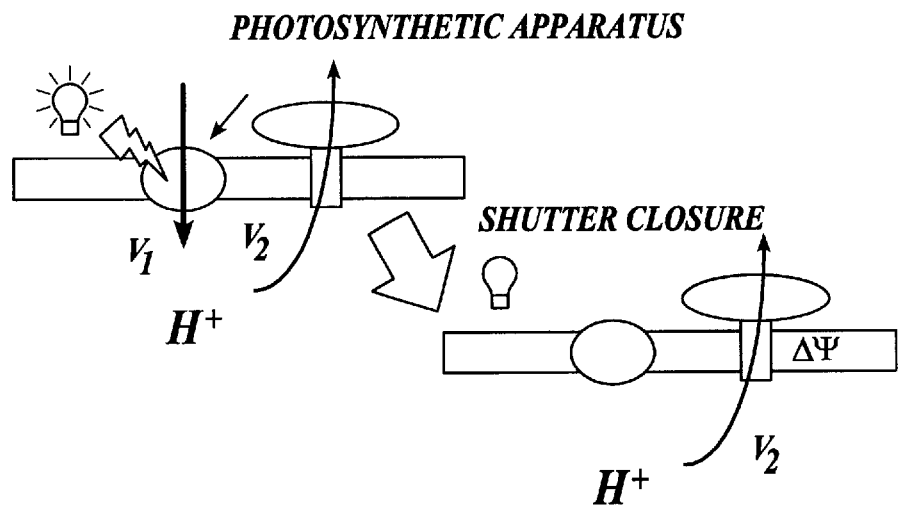
FIG. 9 shows a schematic diagram of the methods of the present invention as applied to the measurement of proton flux.

The methods of the present invention can also be used to measure light-driven fluxes of protons (See FIG. 9). During continuous illumination, protons are pumped across the thylakoid membrane by the photosynthetic electron transport chain and the resulting proton motive force (p.m.f.) is dissipated by the turnover of the ATP synthase and proton leakage pathways (Mitchell P, *Ann. Rev. Biochem.* 46: 996–1005 (1977)). As with the electron transfer reactions discussed above, the flux of protons into the lumen ($v_1$) will be precisely balanced by efflux ($v_2$) in the steady-state. Upon a rapid light-dark transition, the light-driven proton pump ($v_1$) is halted, leaving only proton efflux ($v_2$).

Because protons are charged, their movement across the thylakoid membrane is electrogenic and thus the magnitude of $v_2$ can be measured by changes in the transthylakoid electric field (which is probed by the electrochromic shift). This should hold true even if the steady-state transthylakoid electric field is negated by counter movements of ions (e.g., Vredenberg W J *Biochem. Biophys. Res. Comm.* 42:111–118 (1971); Vredenberg W J and Bulychev A A, *Plant Science Letters* 7:101–107 (1976) and Vredenberg W J and Tonk W J M, *Biochim. Biophys. Acta*, 387:580–587 (1975)) as long as ion fluxes are significantly slower than proton efflux. This appears to be the case, as shown both from microelectrode measurements in vitro (Vredenberg and Tonk (1975), supra) and from electrochromic shift measurements in intact plants (see, e.g., FIG. 6). Thus, the present invention provides for the first time, a non-invasive in vivo assay for light-driven proton fluxes and thus for the measurement of light-driven ATP synthesis.

EXAMPLE 4

Measurement of the "Resistance" to Turnover of Photosynthetic Complexes

Figure 10:
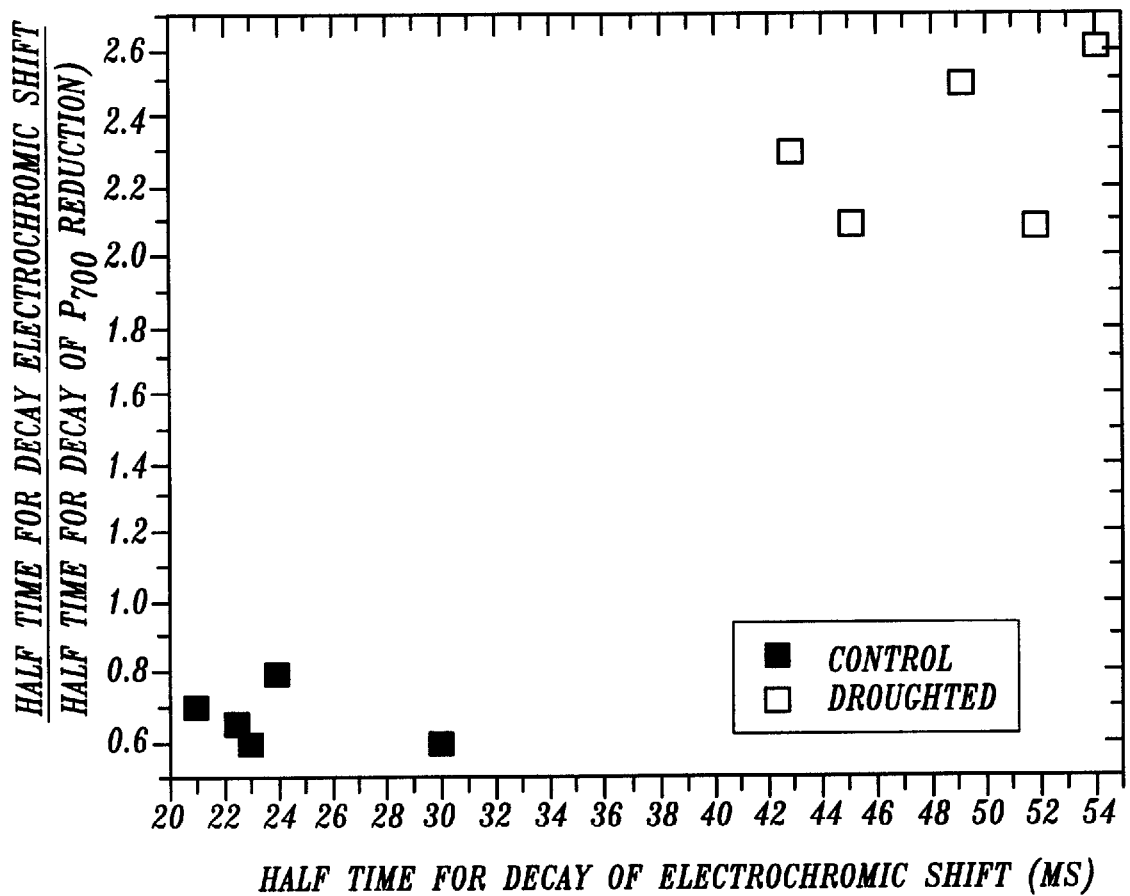
FIG. 10 shows a plot of the ratio of half time for decay of the electrochromic shift to half time for decay of $P_{700}$ reduction versus the half time for decay of the electrochromic shift (measured in milliseconds), as described in Example 4 herein.

The initial rate of the dark-interval relaxation of a number of photosynthetic systems is a measure of the steady-state flux through those systems. The relationship between the amplitude of the relaxation signal with the initial relaxation rate, and the half-time for the relaxation are measures of the "resistance to flux" that can easily be made using the methods of the present invention. FIG. 10 shows data obtained from two tobacco plants after irradiation with 100–1000 mmol photons $m^{-2}s^{-1}$. The control plant was well-watered, while the test plant was deprived of water for two days.

The data in FIG. 10 is plotted as the ratio of the half-time for electrochromic shift decay to the half time for the electron transfer to $P_{700}$ versus the half time for the decay of the electrochromic shift. This way of presenting the data more clearly shows that the resistances to proton pumping (measured by the electrochromic shift) and electron transfer (measured by the 820 nm change) are both increased by drought stress, but that the resistance to proton pumping is affected more strongly than the resistance to electron transfer.

EXAMPLE 5

Measurement of the Efficiency of Light Capture by Photosystem II

The methods of the present invention can also be used to measure the efficiency of light capture by photosystem II. Light capture efficiency is related to antenna regulation, and thus to the physiological status of the plant.

Prior to the present invention this efficiency parameter (termed $\phi_{II}$) was determined using super-saturating pulses of light as the ratio of the change in fluorescence induced by the saturating pulse ($F_v$) over the maximal chlorophyll a fluorescence obtained during the saturating pulse ($F_M$). This requires bulky and expensive light sources and can potentially harm or disturb the plant being measured. The methods of the present invention make this measurement using an alternative approach: by comparing the initial slopes of fluorescence yield, reflecting PS II photochemistry and photochemical efficiency (or antenna downregulation), with absorbance changes at 820 nm, reflecting PS I photochemistry, or 520 nm, reflecting proton pumping.

Figure 11:
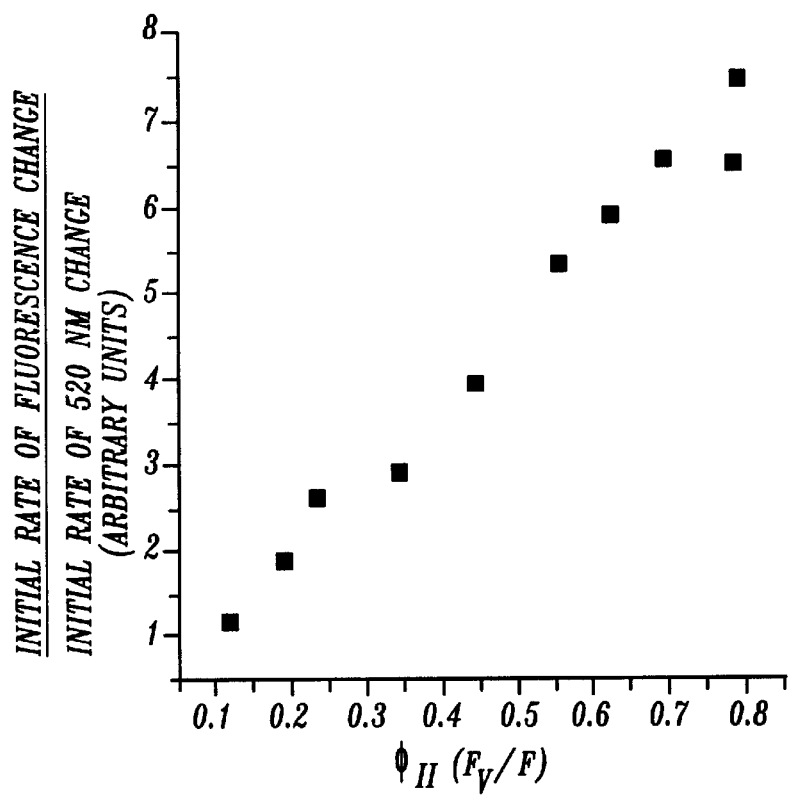
FIG. 11 shows the ratio of initial rates of fluorescence and proton pumping (520 nm absorbance changes) versus $\phi_{II}$ measured in the same leaf over a range of light intensities, as described in Example 5 herein.

FIG. 11 shows data from a greenhouse grown tobacco plant, comparing the ratio of initial rates of fluorescence and proton pumping (520 nm absorbance changes) measured using the methods of the present invention with $\phi_{II}$, measured in the same leaf over a range of light intensities. The $\phi_{II}$ data was obtained by periodically applying saturating light pulses (1 s long, >10,000 μmole photons $m^{-2}s^{-1}$ white light from a xenon arc lamp, filtered to eliminate infrared and ultraviolet radiation). A good correlation was observed indicating that the methods of the present invention can be used to obtain qualitative, and relative, estimates of antenna downregulation.

EXAMPLE 6

Determining the Physiological State of a Plant in Response to Drought Stress The data described in this example show how the methods of the present invention can be used to correlate changes in either of two photosynthetic parameters (ATP synthase activity and $P_{700}$ reduction) to drought stress in plants.

Figure 12:
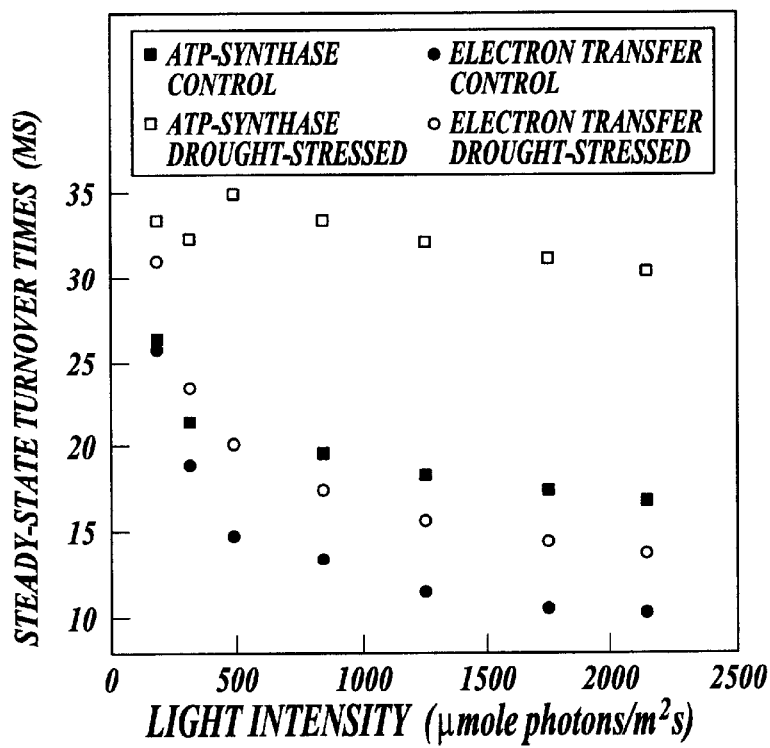
FIG. 12 shows measurements of the relaxation half-times associated with ATP synthesis (i.e. the signal at 520 nm) and $P_{700}$ reduction (i.e. at 820 nm). These measurements were used to measure drought stress in a detached plant leaf as described in Example 6 herein.

FIG. 12 shows measurements of the relaxation half-times for signals associated with ATP synthesis (i.e. the signal at 520 nm) and $P_{700}$ reduction (i.e. at 820 nm) in a drought-stressed plant and in a control plant that was not subjected to drought stress. The data is expressed as the inverse of the relaxation time (or the time it takes to decay to 1/2.718 of the original value). The tobacco plants were grown in a green house in pots. One plant was watered (control), the other was subjected to water stress (drought-stressed) by not watering it for two days.

There was a marked increase in the steady state turnover times, indicating a slowing of electron transfer and ATP synthase activity in response to drought stress.

Figure 13:
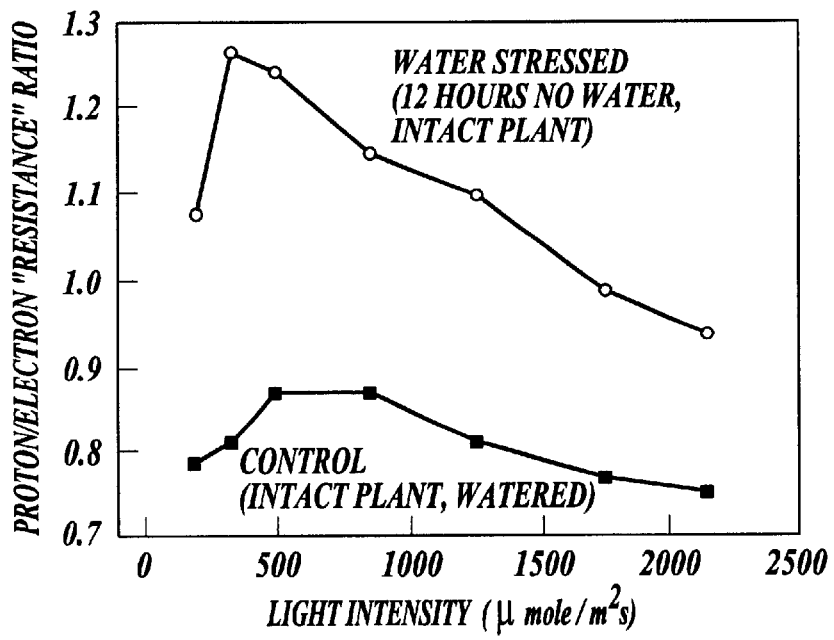
FIG. 13 shows a plot of the ratio of the turnover times of $P_{700}$ to ATP synthase. This plot was generated using the data set forth in FIG. 7.

The reaction of the plants to drought conditions and its effects on photosynthesis is more clearly observed by plotting the ratio of the turnover times of $P_{700}$ to ATP synthase (See FIG. 13), i.e., this ratio, referred to as the proton/electron "resistance" ratio, is higher in drought stressed plants than in unstressed, control plants. The ratio of the two measurements in a control and drought stressed plant shows the ability of the methods of the present invention to distinguish a normal, non-stressed plant from one undergoing drought stress. The advantage of making a ratio is that plant-plant fluctuations can be accounted for, thus allowing an immediate recognition of the stress status of a plant.

EXAMPLE 7

Figure 14:
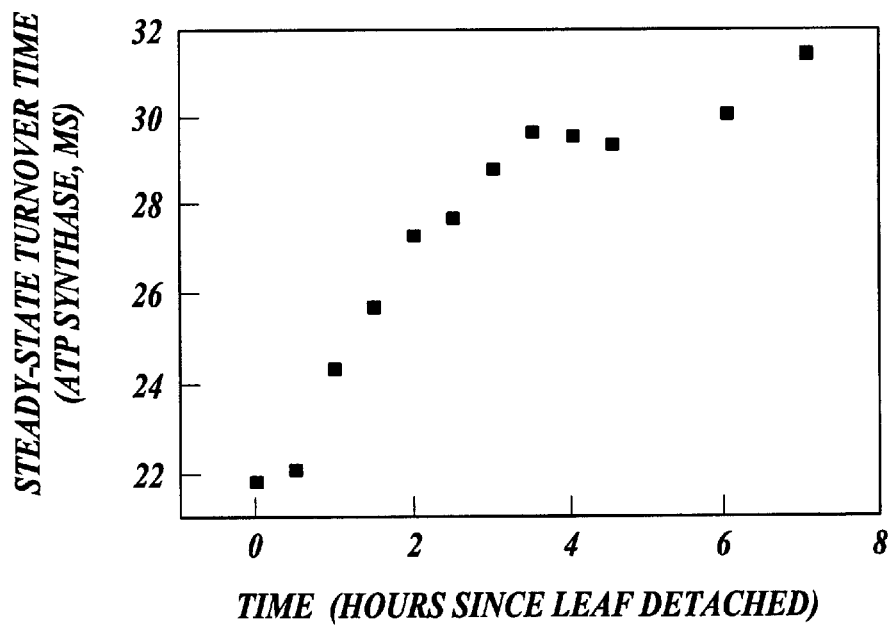
FIG. 14 shows measurement of the ATP synthase reaction as a function of time after detachment of the measured leaf from a plant.

Correlation of the Rate of Change of the ATP Synthase Reaction With Drought Stress FIG. 14 shows measurements of the ATP synthase reaction as a function of time after detachment of the measured leaf from a plant. The half-time for relaxation of the electrochromic shift was measured using diffused-optics flash kinetic spectrophotometer instrument 10 to generate a measuring beam of light at 520 nm. A leaf from an intact tobacco plant was measured, then detached from the plant. Additional measurements were made on the detached leaf over a time course. Detachment of the leaf resulted in the induction of a condition of plant stress (i.e., drought stress) in the leaf. As shown in FIG. 12, the onset of leaf plant stress was reflected in an increase in the relaxation time for the turnover of the ATP synthase. These results showed that the ATP synthase reaction in leaves responded sensitively and rapidly to drought stress.

EXAMPLE 8

Figure 15:
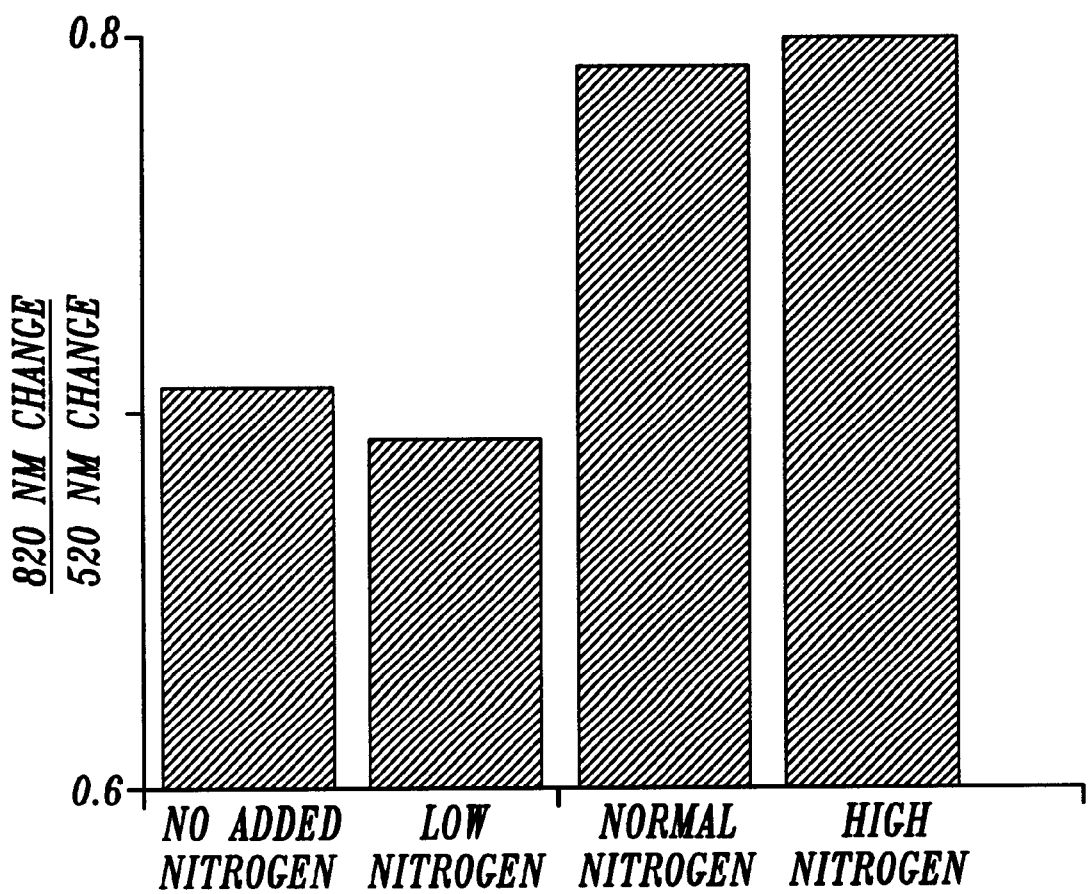
FIG. 15 shows the ratio of the change in the 820 nm signal versus the change in the 520 nm signal in tobacco plants as a function of the availability of nitrogen as a nutrient. The data was obtained from plants exposed to continuous 700 $\mu$mole photons m$^{-2}$s$^{-1}$ light as described in Example 8 herein. The light was shuttered for a period of 200 ms, at which time the absorbance changes were measured.

Response of ATP Synthase/Electron Transfer ($P_{700}$) Resistances to Nitrogen Stress The data set forth in this example and in FIG. 15 show that the ratio of ATP synthase resistance/electron transfer ($P_{700}$) resistance decreases in response to nitrogen stress.

Plants subjected to nitrogen fertilizer deficits exhibited a lowered ratio of ATP synthase resistance/electron transfer ($P_{700}$) resistance, as indicated by a low ratio of the change in the 820 nm signal versus the change in the 520 nm signal (see FIG. 15). This observation is in contrast to the increased ratio observed with drought stressed plants. This observation shows that the methods of the present invention can be used to not only measure plant stress, but distinguish between various kinds of plant stress based upon the ratio of ATP synthase/electron transfer resistances observed in control versus test plants.

EXAMPLE 9

Dark Interval Relaxation Kinetics of Absorbance Changes as a Quantitative Probe of Steady-State Electron Transfer Abbreviations used in this Example: $A_G$—gross carbon assimilation; cyt—cytochrome; DIRK—dark-interval relaxation kinetics; $DIRK_{hpc}$—the initial rate of change, upon shutter closure, of the redox states of all high potential chain components; DOFS—diffused optics flash spectrophotometer; EPR—electron paramagnetic resonance; $E_{hpc}$—the redox poise of the high potential chain; $Fe_2S_2$—the 'Rieske' iron sulfur cluster; hpc—the high potential chain of electron carriers, consisting of cyt f, plastocyanin and $P_{700}$; IR—infrared; IRGA—infrared gas analyzer; KhPC—the equilibrium constant for sharing of electrons between (cyt f+plastocyanin) and $P_{700}$; PC—plastocyanin; PS—photosystem; PQ—plastoquinone; $PQH_2$—plastoquinol; $Q_A$—the primary quinone acceptor of PS II; $Q_o$—the plastoquinol oxidase site of the cytochrome $b_6f$ complex;

Plant material. *Nicotiana tobacum* (tobacco) plants were grown under greenhouse conditions (~900 $\mu$mol photons $m^{-2}s^{-1}$ maximum light intensity). The plants were watered daily and fertilized once a week. Young, fully-expanded, attached leaves were used for all experiments.

Dark interval relaxation kinetics. Steady-state rates of photosynthetic electron transfer were estimated by following the absorbance changes upon rapid light-dark transitions using diffused optics flash spectrophotometer 10. Actinic light intensities ranging from 200 to 1650 $\mu$mol photons $m^{-2}s^{-1}$ of red light were achieved by filtering a high-intensity xenon arc lamp through a series of two dichroic filters (Optical Coatings Inc, Calif.), one cutting off below 600 nm, the other above 750 nm. Dark intervals were achieved by shuttering the light with an electromechanical shutter (Uniblitz™ VS25) with 3.25 ms shutter closure time, synchronized to measuring pulses by the DOFS control computer. Kinetics at each light intensity were averaged over 3 traces with the initial slope measurement beginning less than 2 ms after final shutter closure encompassing 5 data points over 6 ms. Cytochrome f redox changes were measured and deconvoluted as described in Kramer D M, Sacksteder C A (1998) Photosynth Res 56: 103–112. The re-reduction kinetics of $P_{700}^+$ were detected at 820 nm, where the $P_{700}^+$ cation absorbs (Katoh S, Shiratori I, Takamiya A (1962) Biochemistry 51: 32–40). We considered possible interference from other species at 820 nm (Klughammer C, Schreiber U (1991) Z Naturforsch 46c: 233–244; Kramer D M, Crofts A R. (1996) Control of photosynthesis and measurement of photosynthetic reactions in intact plants. In: N Baker, (ed). Photosynthesis and the Environment. Advances in Photosynthesis pp. 25–66. Dordrecht, The Netherlands: Kluwer Academic Press; Klughammer C, Schreiber U. (1998) Measuring $P_{700}$ absorbance changes in the near infrared spectral region with a dual wavelength pule modulation system. In: G Garab, (ed). Photosynthesis: Mechanisms and Effects pp. 4357–4360. Dordrect: Kluwer Academic Publishers), but concluded that over the time range of the initial rate measurements, these species did not significantly compromise the data.

$CO_2$ fixation rates. Carbon exchange and absorbance kinetics were measured simultaneously using an open flow system containing two infrared gas analyzers (IRGAs) in series, an Anarad AR-500-R, set up in differential mode, and a Qubit Systems S151 set up in absolute mode. Similar assimilation measurements were obtained with both detectors while the Qubit IRGA was used to measure absolute $CO_2$ levels. The leaf chamber/gas exchange cuvette was constructed in-house, based on the Qubit Systems design, but with a significantly smaller leaf aperture to accommodate the light path of DOFS instrument 10. Two Plexiglas windows fitted with ports for gas flow were fastened together with a neoprene washer to seal the chamber and protect the leaf. As in the Qubit chamber, the leaf boundary resistance layer was minimized with an array of evenly spaced gas inlet and outlet ports on both sides of the chamber. A premixed, compressed gas mixture containing 350 ppm $CO_2$, 1% $O_2$ and a balance of $N_2$, was flowed through the sample chamber at a constant flow rate of 75 ml·$min^{-1}$. A low flow rate was used because the sample leaf area, 1.7 $cm^2$, was correspondingly small, allowing for better resolution of the $CO_2$ signal changes. The depression in $[CO_2]$ over the leaf was less than 50 ppm under all conditions. A thermocouple wire was used to obtain leaf temperature readings while the Qubit system sensors were used to monitor air temperature and humidity. The $CO_2$, temperature and humidity data were collected using the Qubit systems Universal Lab interface and Logger Pro Software (Vernier). The air in the leaf chamber was maintained at average temperature and relative humidity of 23° C. and 62% respectively. Gross $CO_2$ assimilation ($A_G$) was calculated as the difference of light and dark $CO_2$ uptake measurements. Respiration during photosynthesis was estimated using the earliest stable dark respiration rate directly following each illumination interval.

Figure 16A:
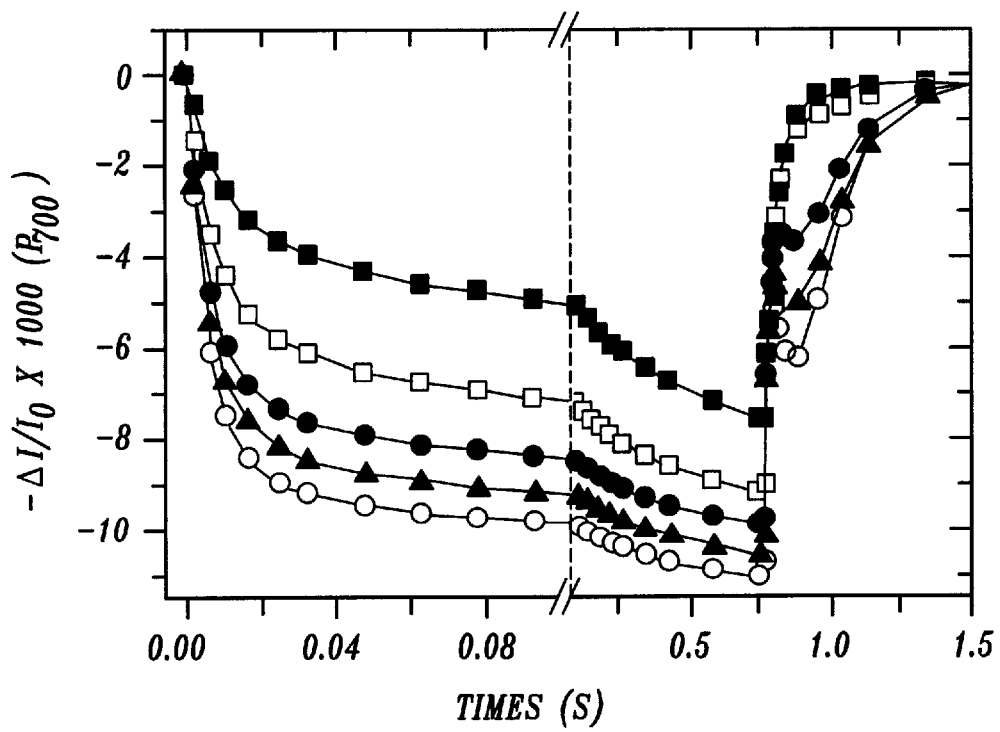
FIG. 16A shows dark interval relaxation kinetics of $P_{700}$ in an intact tobacco leaf illuminated adapted for at least 30 minutes at 145 (closed squares), 310 (open squares), 470 (closed circles), 700 (open circles) and 1050 (closed triangles) $\mu$mol photons m$^{-2}$s$^{-1}$ red light, followed by a series of 750 ms dark intervals, taken at 60 s intervals. Data was taken and deconvoluted as described in Example 9 herein.
Figure 16B:
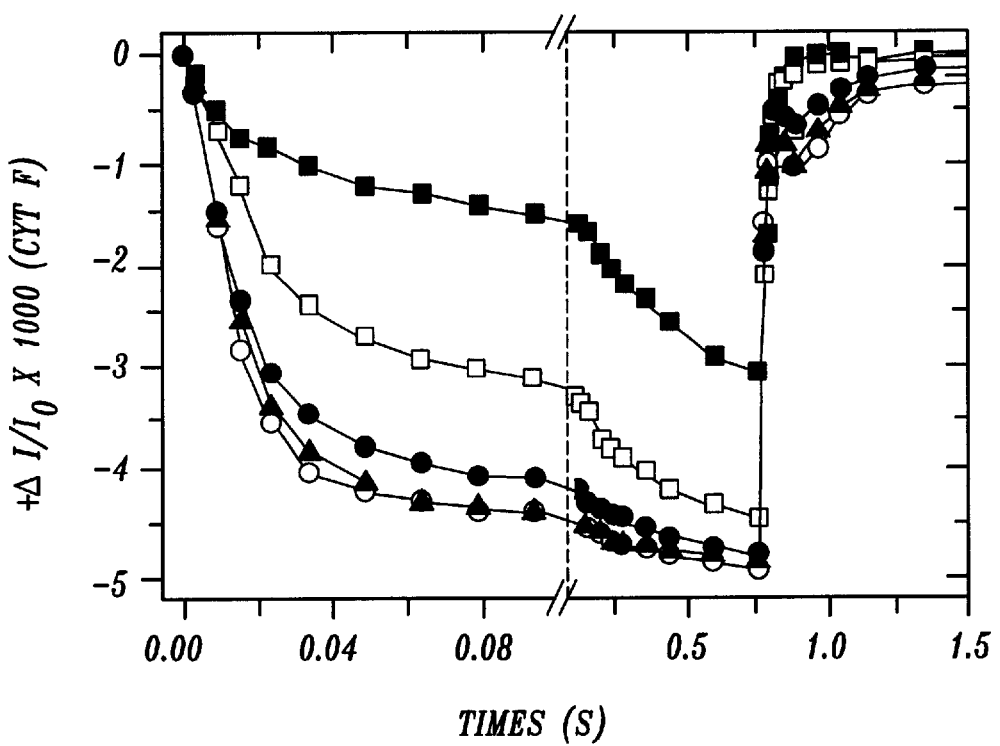
FIG. 16B shows dark interval relaxation kinetics of cyt f in an intact tobacco leaf illuminated adapted for at least 30 minutes at 145 (closed squares), 310 (open squares), 470 (closed circles), 700 (open circles) and 1050 (closed triangles) $\mu$mol photons m$^{-2}$s$^{-1}$ red light, followed by a series of 750 ms dark intervals, taken at 60 s intervals. Data was taken and deconvoluted as described in Example 9 herein.

Analysis of dark-interval relaxation kinetics in intact leaves under steady-state illumination FIG. 16A and FIG. 16B show DIRK traces, with a dark interval of 750 ms, for $P_{700}$ (820 nm) and cyt f respectively in an attached tobacco leaf under steady-state light conditions. During the first 100 ms, the time course over which this type of analysis is typically taken, the re-reduction of both $P_{700}$ and cyt f appeared essentially monophasic. The half times changed little with increasing light intensity, varying from 11 ms to 6 ms for $P_{700}$ and 18 ms to 13 ms for cyt f as light intensity was changed from 145 to 1050 $\mu$mol·$m^{-2}$·$s^{-1}$. These data are consistent with that observed previously by several groups (Harbinson J, Hedley C L (1989) Plant Cell Environ 12: 357–369; Laisk A, Oja V (1994) Photosynth Res 39: 39–50; Laisk A, Oja V (1995) Photosynth Res 45: 11–19; Kramer D M, Sacksteder C A, Cruz J A (1999) Photosynth Res 60: 151–163; Ott T, Clarke J, Birks K, Johnson G (1999) Planta 209: 250–258). A significantly slower phase in the reduction kinetics for both $P_{700}$ and cyt f appears when the decay over the longer, 750 ms, dark interval was considered. It is possible that a fraction of the long phase of the 820 nm absorbance kinetics is due to re-reduction of PC or to light scattering changes (Klughammer C, Schreiber U (1991) Z Naturforsch 46c: 233–244). However, this is not likely to be the case with cyt f because extensive spectral analysis (as described in Kramer D M, Sacksteder C A (1998) Photosynth Res 56: 103–112) showed that the cyt f signal is essentially uncontaminated by other contributions (not shown). The slow phases of $P_{700}$ and cyt f reduction may be due to a relative imbalance in the excitation of PS I over PS II, resulting in a relatively small extent of PQ pool reduction. The apparent pseudo-first order behavior of the initial kinetics of the rapid (10–20 ms) re-reduction phase can be explained by a preferential binding of $PQH_2$ over PQ to the $Q_o$ site (as proposed in Kramer D M, Joliot, A., Joliot, P., Crofts, A. R. (1994) Biochim Biophys Acta: 251–262), ensuring that the cyt $b_6f$ complex will be at least partially charged with quinol substrate even with a relatively oxidized quinone pool. Bound $PQH_2$ will be rapidly oxidized upon a light-dark transition, giving rise to the rapid phase. If the PQ pool is predominantly oxidized, the binding of fresh $PQH_2$ to the $Q_o$ site will be slow or inhibited, resulting in the slower reduction phase.

DIRK estimates of flux using the summation method. The summation method was used to account for differential partitioning of electrons. The total number of electrons entering the hpc over a particular time period, $\Delta[hpc(red)]$, is defined as:

$$\Delta[hpc(red)] = \sum_{i=1}^{n} \frac{\Delta A_{i,\lambda}}{\Delta E_{i,\lambda}}$$

where n is the number of species in the hpc, $\Delta A_{i,\lambda}$ is the absorbance change at a particular wavelength due to the reduction of species i at wavelength or set of wavelengths $\lambda$, and $\Delta E_{i,\lambda}$ is the effective reduced-minus-oxidized difference extinction coefficient at $\lambda$, which includes scatter-induced enhancement and flattening effects. As discussed above, we assume that PC and cyt f are nearly isopotential and rapidly equilibrating, allowing us to treat them as a single redox pool. Previous measurements (Graan T, Ort D R (1984) J Biol Chem 259: 14003–14010; Hope A B (1993) Biochim Biophys Acta 1143: 1–22) indicate that the ratio of PC:cyt f:$P_{700}$ is approximately 2:1:1, and thus, the total hpc redox changes (i.e., $\Delta[hpc(red)]$), as measured by the spectroscopically accessible redox changes of cyt f and $P_{700}$, can be described by the following:

$$\Delta[hpc(red)] = 3\left(\frac{\Delta A_{cytf}}{\Delta E_{cytf}}\right) + \frac{\Delta A_{820}}{\Delta E_{P_{700}}}$$

where $\Delta A_{cyt}$ f represents the deconvoluted absorbance change for cyt f using wavelengths around its alpha band. If the effective extinction coefficients are accurate, the initial rate of change of $\Delta[hpc(red)]$ upon shutter closure, termed here $DIRK_{hpc}$, should be equal to the rate of electron transfer through the photosynthetic electron transfer chain.

There are a number of factors that alter the effective extinction coefficient, particularly flattening and scattering-induced enhancement (see Latimer P, Eubanks C A H (1962) Arch Biochem Biophys 98: 274–285; Klughammer C, Schreiber U (1991) Z Naturforsch 46c: 233–244; Kramer D M, Crofts A R. (1996) Control of photosynthesis and measurement of photosynthetic reactions in intact plants. In: N Baker, (ed). Photosynthesis and the Environment. Advances in Photosynthesis pp. 25–66. Dordrecht, The Netherlands: Kluwer Academic Press). It is therefore necessary to estimate their values in situ. To accomplish this, absorbance changes were measured that are associated with both cyt f and $P_{700}$ (at 820 nm) redox changes that occurred upon full oxidation of hpc components by exposure to 60 seconds of far red (>730 nm) light. This was judged to give essentially full oxidation of hpc components since increased intensities resulted in no increase in the signal extents.

Reported values for the extinction coefficient for the alpha band of cyt f at 554 nm ($\epsilon_{cyt\,f}$) range between 19.5 $mM^{-1}cm^{-1}$ in parsley and lettuce (Forti M L, Bertolé G, Zanetti G (1965) Biochim Biophys Acta 109: 33–40; Nelson N, Neumann J (1972) J Biol Chem 247: 1817–1824) and 25 $mM^{-1}cm^{-1}$ in spinach by Metzger S U, Cramer W A, Whitmarsh J (1997) Biochim Biophys Acta 1319: 233–241. Nishio and Whitmarsh have found that the effective extinction coefficient for the alpha band of cyt f in leaves is nearly identical to that found in isolated membrane, i.e., it appears relatively uncorrupted by flattening and scatter-induced enhancement. We thus converted our absorbance changes to concentrations using two values, the newer value (Metzger S U, Cramer W A, Whitmarsh J (1997) Biochim Biophys Acta 1319: 233–241) and the average of the older and the newer. When adjusted to reflect our method of deconvolution, these resulted in effective extinction coefficients for cyt f of 21.9 and 19.5 $mM^{-1}cm^{-1}$ respectively. From this, and a ca. 1:1 stoichiometry for cyt f and $P_{700}$ (e.g., Graan T, Ort D R (1984) J Biol Chem 259: 14003–14010; Kramer D M (1990). Ph.D. Thesis thesis. University of Illinois, Urbana, Ill.), effective extinction coefficients of 121 and 108 $mM^{-1}cm^{-1}$ for $P_{700}$ were estimated. These estimates do not include possible contributions of PC oxidation to the 820 nm absorbance change of up to 30% (Klughammer C, Schreiber U (1991) Z Naturforsch 46c: 233–244). However, altering the relative extinction coefficient of $P_{700}$ by 30% had only small effects on the linearity DIRK initial rates vs. $A_G$, although it did affect the slope of this relationship. In addition, key experiments were repeated using an alternate method for the calculation of the hpc in which contributions from PC reduction were independently estimated from near IR absorbance changes as reported by Klughammer and Schreiber (Klughammer C, Schreiber U (1991) Z Naturforsch 46c: 233–244; Klughammer C, Schreiber U. (1998) Measuring $P_{700}$ absorbance changes in the near infrared spectral region with a dual wavelength pule modulation system. In: G Garab, (ed). Photosynthesis: Mechanisms and Effects pp. 4357–4360. Dordrect: Kluwer Academic Publishers). This approach also yielded linear data, very similar to that where PC redox changes were estimated from cyt f absorbance changes. In this way it is also possible to make DIRK measurements exclusively in the near infrared. The IR approach has significant advantages from an instrumentation standpoint, because these wavelengths are non-actinic and intense light-emitting diodes in this spectral range are readily available. For the purposes of the experiments reported herein, cyt f was used because the effective extinction coefficient in leaves is most likely close to published values from isolated material, allowing quantitative estimates of electron flux to be made.

Figure 17:
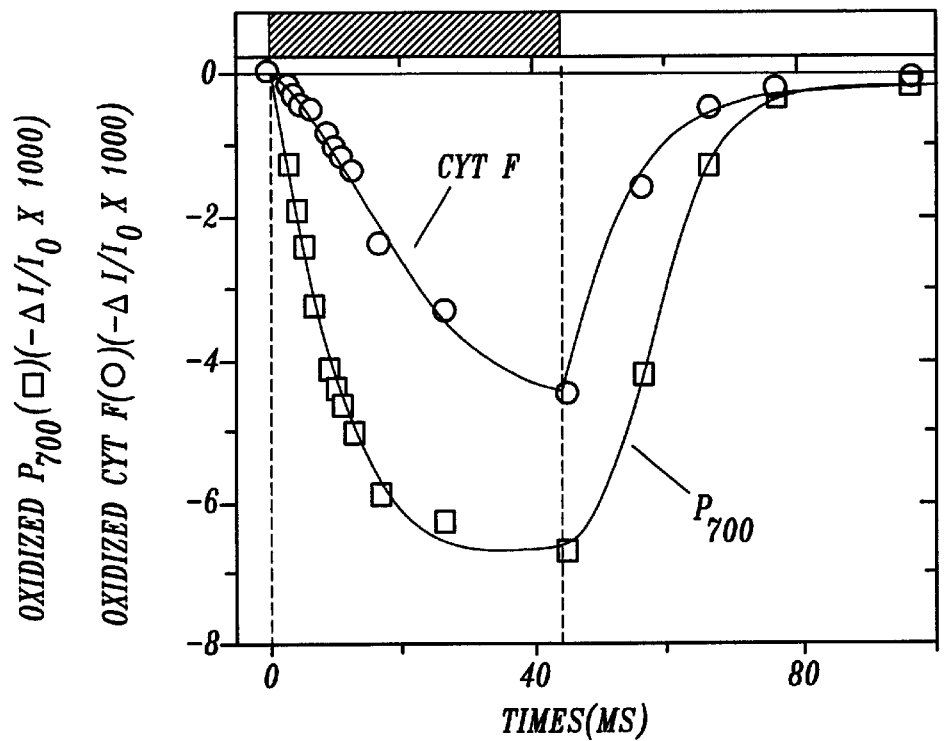
FIG. 17 shows short dark interval relaxation kinetics of $P_{700}$ (squares) and cyt f (circles) in an intact tobacco leaf illuminated for at least 30 minutes at 940 $\mu$mol photons m$^{-2}$s$^{-1}$ red light, followed by a series of 40 ms dark intervals, taken at 10 s intervals. Data was taken and deconvoluted as described in Example 9 herein.

DIRK analysis of linear electron transfer. For comparison with results from DIRK analysis $CO_2$ assimilation ($A_G$) under non-photorespiratory conditions (i.e., low oxygen) was measured. To avoid perturbation of steady-state electron transfer rates, the dark intervals were kept short (40 ms). Representative kinetic traces, taken at 940 $\mu$mol photons $m^{-2}s-1$ are shown in FIG. 17. The sigmoidal reduction kinetics of cyt f (upon shutter closure) and oxidation kinetics of $P_{700}$ (upon shutter opening) indicate that $K_{hpc}$>1 and confirm the necessity of accounting for differential electron partitioning.

Figure 18:
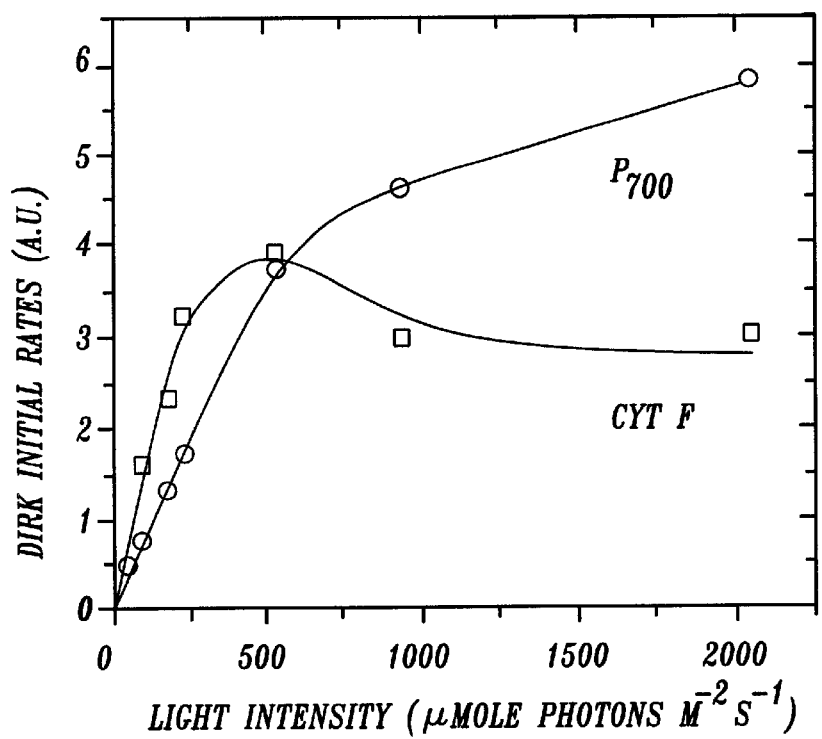
FIG. 18 shows the dependence of DIRK initial rates for cyt f and $P_{700}$ on light intensity. The initial rates of DIRK for cyt f (open squares) and $P_{700}$ (open circles) were obtained from data under conditions in FIG. 17, except that the light intensity was varied from 13 to 2100 $\mu$mol photons m$^{-2}$s$^{-1}$.

FIG. 18 shows the light-intensity dependence of DIRK initial rates of cyt f and $P_{700}$ reduction. Both cyt f and $P_{700}$ DIRK rates were nearly linear with light intensities between 0 and 250 $\mu$mol photons $m^{-2}s^{-1}$. At about 500 $\mu$mol photons $m^{-2}s^{-1}$, cyt f DIRK reached a maximum, above which it fell, reflecting the appearance of the distinct lag phase in cyt f reduction (as seen in FIG. 17). On the other hand, DIRK of $P_{700}$ continued to rise, nearing saturation at the highest light intensity. This behavior could be explained by differential partitioning effects.

Figure 19:
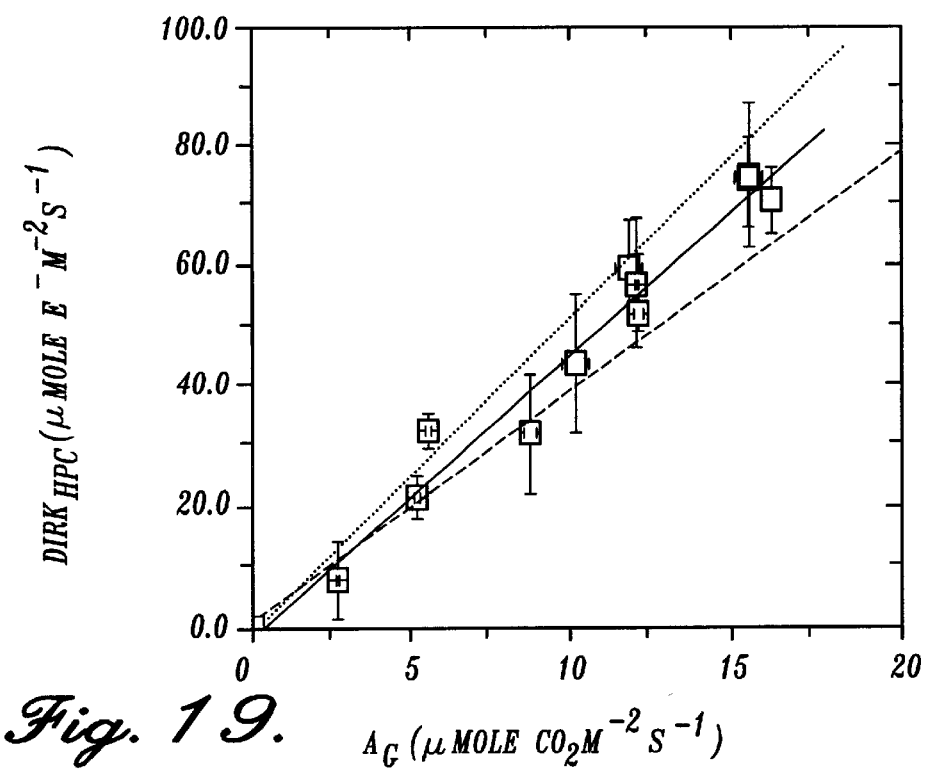
FIG. 19 shows the DIRK initial rates for reduction of the hpc as a function of $A_G$. DIRK initial rates of reduction of the entire hpc were calculated from those for cyt f and $P_{700}$ as described in Example 9. Gross $CO_2$ assimilation (AG) was measured as described in Example 9. The error bars represent the standard deviation of measured values at each light intensity. The solid line represents the best fit line, with a slope of 4.8 e$^-$/$CO_2$ (r=0.98). The dashed line represents the expected relationship, i.e., four e$^-$ per $CO_2$.

FIG. 19 shows that $DIRK_{hpc}$, i.e., the total hpc reduction rates of all hpc components, is linearly dependent on $A_G$ over light intensities from ~10% to essentially fully saturating. The symbols represent $DIRK_{hpc}$ values derived using the extinction coefficient of Metzger S U, Cramer W A, Whitmarsh J (1997) Biochim Biophys Acta 1319: 233–241. Within the noise level, the dependence of $DIRK_{hpc}$ initial rate on $A_G$ was linear and a best-fit line (FIG. 19, solid line) gave an r-value of 0.98 with a y-intercept near zero. The slope of this line gave an estimated 4.8 electrons per $CO_2$ fixed. Not surprisingly, the slope was sensitive to chosen cyt f extinction coefficients. When the average of literature values was used, an estimate was obtained of 5.4 electrons passed through the hpc per $CO_2$ fixed (FIG. 19, dotted line). The dashed line in FIG. 19 indicates the expected value of 4 electrons passed through the hpc per $CO_2$ fixed. Given the good correspondence between estimated and predicted $e^-:CO_2$ ratio, it was concluded that light-dependent partitioning of electrons can be well accounted for by the summation technique.

The ca. 15–20% deviation in electron and $CO_2$ measurements can be ascribed to errors in the estimates of effective extinction coefficients, the stoichiometry of PC to cyt f, contributions of PC to the 820 nm signal, or in the measurement of $A_G$. For example, an effective extinction coefficient for cyt f alpha band of 30 $mM^{-1}cm^{-1}$ resulted in a ratio of 4 for electrons per $CO_2$ fixed. On the other hand, an excess of hpc electron flux over $A_G$ could be an indicator of significant flux to alternative electron acceptors, including residual photorespiration and nitrite reduction, or of the participation of PS I cyclic electron transfer or the Mehler-peroxidase/water-water cycle (see reviews in Baker N R, Oxborough K, Andrews J R. (1995) Operation of an alternate electron transfer acceptor to $CO_2$ in maize crops during periods of low temperatures. In: P Mathis, (ed). Photosynthesis: From Light to Biosphere pp. 771–776. The Netherlands: Kluwer Academic Publishers; Heber U, Gerst U, Krieger A, Neimanis S, Kobayashi Y (1995) Photosynth Res 46: 269–275; Asada K. (1996) Radical production and scavenging in the chloroplasts. In: N R Baker, (ed). Photosynthesis and the Environment pp. 123–150. The Netherlands: Kluwer Academic Publishers; Kramer D M, Crofts A R. (1996) Control of photosynthesis and measurement of photosynthetic reactions in intact plants. In: N Baker, (ed). Photosynthesis and the Environment. Advances in Photosynthesis pp. 25–66. Dordrecht, The Netherlands: Kluwer Academic Press; Ivanov B, Kobayashi Y, Bukhov N G, Heber U (1998) Photosynth Res 57: 61–70; Cornic G, Bukhov N G, Wiese C, Bligny R, Heber U (2000) Planta 210: 468–477; Eichelmann H, Laisk A (2000) Plant Cell Physiol 41: 138–147; Miyake C, Yokota A (2000) Plant Cell Physiol 41: 335–343). The fact that a linear relationship was observed between $DIRK_{hpc}$ and $A_G$ would indicate that the magnitude of such fluxes were proportional to linear electron transfer (reviewed in Kramer D M, Crofts A R. (1996) Control of photosynthesis and measurement of photosynthetic reactions in intact plants. In: N Baker, (ed). Photosynthesis and the Environment. Advances in Photosynthesis pp. 25–66. Dordrecht, The Netherlands: Kluwer Academic Press).

The DIRK approach is particularly useful under conditions where $CO_2$ and $O_2$ gas exchange estimates are not readily achieved or are significantly affected by alternate electron sinks (e.g., cyclic electron transfer or photorespiration). Moreover, neither the use of saturation pulses nor knowledge of the amount of light absorbed by the plant—both of which are required for the chlorophyll fluorescence techniques—are required for DIRK flux estimates.

EXAMPLE 10

Measurement of Proton Transfer Using the Methods of the Invention

Abbreviations: $A_G$, the rate of gross photosynthetic $CO_2$ assimilation; ATPase, $(C)F_o$–$(C)F_1$ ATP synthase; cyt, cytochrome; DIRK, dark interval relaxation kinetics; $DIRK_{hpc}$, DIRK analysis of absorbance changes associated with reduction of cyt f and $P_{700}$ yielding an estimate of electron flux through the high potential chain of photosynthesis; $DIRK_{ECS}$, DIRK analysis of absorbance changes associated with the ECS yielding an estimate of light-induced proton fluxes through the ATPase; DOFS, diffused optics flash spectrophotometer; ECS, the electrochromic shifting of light-harvesting pigments in response to delocalized transthylakoid electric field; $F_s$, the steady-state chlorophyll a fluorescence yield; $F_M$, the maximal chlorophyll a fluorescence yield obtained under conditions in which non-photochemical fluorescence quenching is minimal; $F_M'$, the yield of chlorophyll a fluorescence obtained during steady-state illumination, during application of light pulses that saturate PS II photochemistry; $H^+/e^-$, the stoichiometry of protons to electrons passed through the photosynthetic apparatus; pmf, proton motive force; PS, photosystem; $\phi_{II}$, the quantum efficiency of PS II and associated antenna; $q_{NP}$, non-photochemical quenching of chlorophyll a fluorescence.

Plants and growth conditions. *Nicotiana tabacum* (tobacco) was grown in a greenhouse with midday light intensity of about 900 $\mu$moles photons $m^{-2}s^{-1}$, as described in Example 9.

Measurements of absorbance changes in the steady-state. Steady-state rates of photosynthetic electron transfer and proton flux through the ATPase were estimated by following the absorbance changes upon rapid light-to-dark transitions using the methods of the invention. Use of DOFS instrument 10 significantly attenuates the interfering light scattering changes in the 500–560 nm range, allowing observation of changes in the redox states of cyt f and $P_{700}$ as well as changes in the extent of the ECS. Wavelength selection was provided by a wheel of 2 or 3 nm bandpass interference filters (Omega Optical, Brattleboro, Vt.) under computer control. Actinic light was provided by a 500 W Xenon arc lamp, collimated with quartz lenses. A series of three aluminum discs for holding optical filters were mounted on computer-controlled servo motors and placed in the light path of the high xenon actinic light. One of these filter discs held a series of two dichroic filters (passing light from 640 to 730 nm, Omega Optical, Brattleboro, Vt.), while the other two held a series of neutral density filters (New Focus, Santa Clara, Calif.). A heat reflecting filter (57401, Oriel, Corp., Stratford, Conn.) was kept in place at all times to remove excess heat from the actinic beam and to prevent saturation of the detectors. The control computer automatically selected actinic light intensities from about 15 to >2010 $\mu$moles photons $m^{-2}s^{-1}$ by switching the neutral density filter combinations.

Young, fully expanded, intact leaves were gently clamped into the leaf chamber of DOFS instrument 10, which was perforated with two 5 mm diameter air holes to allow free exchange of gasses. At least 3 minutes was allowed to establish steady-state conditions after each change in illumination intensity. After steady-state conditions were established, the actinic beam was shuttered for approximately 40 ms periods at 15 s intervals to allow decay of photo-activated processes, and the associated absorbance changes were measured at a range of wavelengths. The actinic light was shuttered (half-time for closure of approximately 3.4 ms) using an electromechanical shutter (Uniblitz, Vincent and Associates). Selected measurements were also performed with a smaller shutter that closed with a half time of ca. 0.5 ms, but allowing for less light throughput, with nearly identical results (not shown). During measurements in the 500–575 nm region, the detectors were protected from actinic light and fluorescence by Schott BG-18 filters, whereas in the case of infrared-measurements, protection was provided by Schott RG730 filters. The blocking filters were mounted on metal discs and positioned by computer control via servo motors. The detector circuit was AC-filtered and thus sensitive to the pulsed measuring beam but not to offsets due to changes in chlorophyll fluorescence or to leakage of actinic light through the filters. The temperature of the leaves, measured by a thermocouple, deviated from room temperature by less than 1° C. during the experiments.

Deconvolution of redox and electrochromic signals. In order to measure relative changes in the transthylakoid electric field, $\Delta\Psi$, generated by movement of protons through the ATPase, changes in the ECS were measured that followed rapid shuttering of the actinic light. To ensure that interfering signals did not affect the results, several different estimates of the electrochromic shift were compared, including the straight $-\Delta/I_0$ changes at 520 or 515 nm, and $-\Delta/I_0$ differences between the following wavelength pairs: 515–545 nm, 520–530 nm, 520–510 nm, and 510–500 nm. For the relatively rapid changes reported in this example, all estimates were found to be proportional within the noise levels, and changes at 520 nm were used throughout. Cytochrome f redox changes were deconvoluted from the electrochromic shift and other background signals by the method described in Kramer, D. M. & Sacksteder, C. A. (1998) *Photosynth. Res.* 56, 103–112, and in Joliot, P. & Joliot, A. (1984) *Biochim. Biophys. Acta* 765, 219–226. The re-reduction kinetics of $P_{700}^+$ were followed by observing the absorbance changes at 820 nm (Katoh, S., Shiratori, I. & Takamiya, A. (1962) *Biochem.* 51, 32–40) as described in Example 9.

Saturation-pulse fluorescence changes. DOFS instrument 10 was modified to measure saturation pulse fluorescence changes. Saturation pulses of either 9000 or 5500 μmoles photons $m^{-2}s^{-1}$ white light lasting ca. 2 s were achieved by removing, by computer control, both the red and neutral density filters from the actinic light path. Full saturation was assumed because both pulse intensities gave essentially identical results. The time required for switching all filters was between 100 and 200 ms, depending upon starting and ending servo positions. Chlorophyll a fluorescence yield changes were measured essentially as in Kramer, D. M., Robinson, H. R. & Crofts, A. R. (1990) *Photosynth. Res.* 26, 181–193, but using the DOFS optics and detector 10. The pulsed measuring beam, which struck the adaxial side of the leaf where the actinic beam struck, consisted of the DOFS xenon measuring flash blocked with a 425 nm (5 nm bandpass) interference filter (Omega Optical, Brattleboro, Vt.) and an infrared rejecting filter (51962, Oriel Corp., Stratford Conn.). Fluorescence was measured on the abaxial side of the leaf with the DOFS sample detector. To minimize the effects of fluorescence re-absorption, the detector was blocked with a color glass filter that transmitted above 750 nm, where chlorophyll absorption is minimal (Vogelmann, T. C., Bomman, J. F. & Josserand, S. (1989) *Phil. Trans. R. Soc. Lond.* 323, 411–421). Steady-state fluorescence yields, $F_s$ were taken just prior to application of saturation pulses, while fluorescence yields with all PS II centers closed, $F_M'$, were taken during the saturation pulse. The parameter $\phi_{II}$ was calculated as $(F_M'-F_s)/F_M'$ (Genty, B., Harbinson, J., Briantais, J.-M. & Baker, N. R. (1990) *Photosynth. Res.* 25, 249–257).

Saturation pulse fluorescence assays of PS II electron transfer rates. Electron transfer flux through PS II was estimated by the saturation-pulse fluorescence rise technique introduced by Genty et al. (Genty, B., Harbinson, J., Briantais, J.-M. & Baker, N. R. (1990) *Photosynth. Res.* 25, 249–257). The application of supersaturating pulses of light saturates all photochemical reaction centers, and changes in chlorophyll a fluorescence yield reflect the photochemical quantum efficiency of PS II associated antenna ($\phi_{II}$) (e.g. Genty, B. & Harbinson, J. (1996) in *Photosynthesis and the Environment*, ed. Baker, N. R. (Kluwer Academic Publishers, The Netherlands), pp. 67–99). Multiplying $\phi_{II}$ by the absorbed actinic light intensity has been shown to yield a good estimate of photosynthetic electron transfer rates (see e.g. Genty, B. & Harbinson, J. (1996) in *Photosynthesis and the Environment*, ed. Baker, N. R. (Kluwer Academic Publishers, The Netherlands), pp. 67–99; Genty, B., Harbinson, J., Briantais, J.-M. & Baker, N. R. (1990) *Photosynth. Res.* 25, 249–257; Falkowski, P. G., Kolber, Z. & Mauzerall, D. (1994) *Biophys. J.* 66, 923–928; Havaux, M., Strasser, R. J. & Greppin, H. (1991) *Photosynth. Res.* 27, 41–55; Krause, G. H. & Weis, E. (1991) *Annu. Rev. Plant Physiol. Plant Mol. Biol.* 42, 313–349; Genty, B., Harbinson, J. & Baker, N. R. (1990) *Plant Physiol. Biochem.* 28, 1–10; Govindjee (1995) *Aust. J. Plant Physiol.* 22, 20–29; Joshi, M. K. & Mohanty, P. (1995) *J. Scient. Ind. Res.* 54, 155–174; Edwards, G. E. & Baker, N. R. (1993) *Photosynth. Res.* 37, 89–102; Edwards, G. E., Johnson, E., Lal, A. & Krall, J. P. (1993) *Plant Cell Physiol.* 34, 1205–1212; Baker, N. R. (1996) in *Photosynthesis and the Environment*, ed. Baker, N. R. (Kluwer Academic Press, The Netherlands), pp. 469–476). In the experiments reported herein, we multiplied $\phi_{II}$ by the incident light intensity which provides, in arbitrary units, a measure of PSII electron flux.

It is noteworthy that, under extreme conditions, estimates of electron flux derived from $\phi_{II}$ have sometimes deviated from those derived from alternative techniques, e.g. $CO_2$ measurements (reviewed in Baker, N. R. (1996) in *Photosynthesis and the Environment*, ed. Baker, N. R. (Kluwer Academic Press, The Netherlands), pp. 469–476; Baker, N. R., Oxborough, K. & Andrews, J. R. (1995) in *Photosynthesis: From Light to Biosphere*, ed. Mathis, P. (Kluwer Academic Publishers, The Netherlands), Vol. IV, pp. 771–776; Kramer, D. M. & Crofts, A. R. (1996) in *Photosynthesis and the Environment. Advances in Photosynthesis*, ed. Baker, N. (Kluwer Academic Press, Dordrecht, The Netherlands), pp. 25–66). It has been argued that, in some cases, these deviations may be due to secondary effects of high-intensity light pulses on other properties of the system (van Gorkom, H. J., Tamminga, J. J. & Havema, J. (1974) *Biochim. Biophys. Acta* 347, 417–438; Vemotte, C., Etienne, A. L. & Briantais, J. M. (1979) *Biochim. Biophys. Acta* 545, 519–527; Kramer, D. M., DiMarco, G. & Loreto, F. (1995) in *Photosynthesis: From Light to Biosphere*, ed. Mathis, P. (Kluwer Academic Publishers, The Netherlands), Vol. I, pp. 147–150; Samson, G. & Bruce, D. (1996) *Biochim. Biophys. Acta* 1276, 147–153; Haveman, J. & Mathis, P. (1976) *Biochim. Biophys. Acta* 440, 346–355; Best, J. A. V. & Mathis, P. (1978) *Biochim. Biophys. Acta* 503, 178–188) or from the operation of alternative electron acceptors or cycles around one or the other photosystems (e.g. Ivanov, B., Kobayashi, Y., Bukhov, N. G. & Heber, U. (1998) *Photosynth. Res.* 57, 61–70; Comic, G., Bukhov, N. G., Wiese, C., Bligny, R. & Heber, U. (2000) *Planta* 210, 468–477; Heber, U., Gerst, U., Krieger, A., Neimanis, S. & Kobayashi, Y. (1995) *Photosynth. Res.* 46, 269–275; Baker, N. R., Oxborough, K. & Andrews, J. R. (1995) in *Photosynthesis: From Light to Biosphere*, ed. Mathis, P. (Kluwer Academic Publishers, The Netherlands), Vol. IV, pp. 771–776;

Peterson, R. B. (1991) *Plant Physiol.* 97, 1388–1394; Foyer, C., Furbank, R., Harbinson, J. & Horton, P. (1990) *Photosynth. Res.* 25, 83–100; Foyer, C. H., Lelandais, M. & Harbinson, J. (1992) *Plant Physiol.* 99, 979–986; Harbinson, J. & Foyer, C. H. (1991) *Plant Physiol.* 97, 41–49; Klughammer, C. & Schreiber, U. (1994) Planta 192, 261–268; Asada, K. (1996) in *Photosynthesis and the Environment*, ed. Baker, N. R. (Kluwer Academic Publishers, The Netherlands), pp. 123–150; Eichelmann, H. & Laisk , A. (2000) *Plant Cell Physiol* 41, 138–147; Miyake, C. & Yokota, A. (2000) *Plant Cell Physiol* 41, 335–343). All experiments in this example were performed under permissive, non-stressed conditions, and so interference from such phenomena should not occur.

Figure 20:
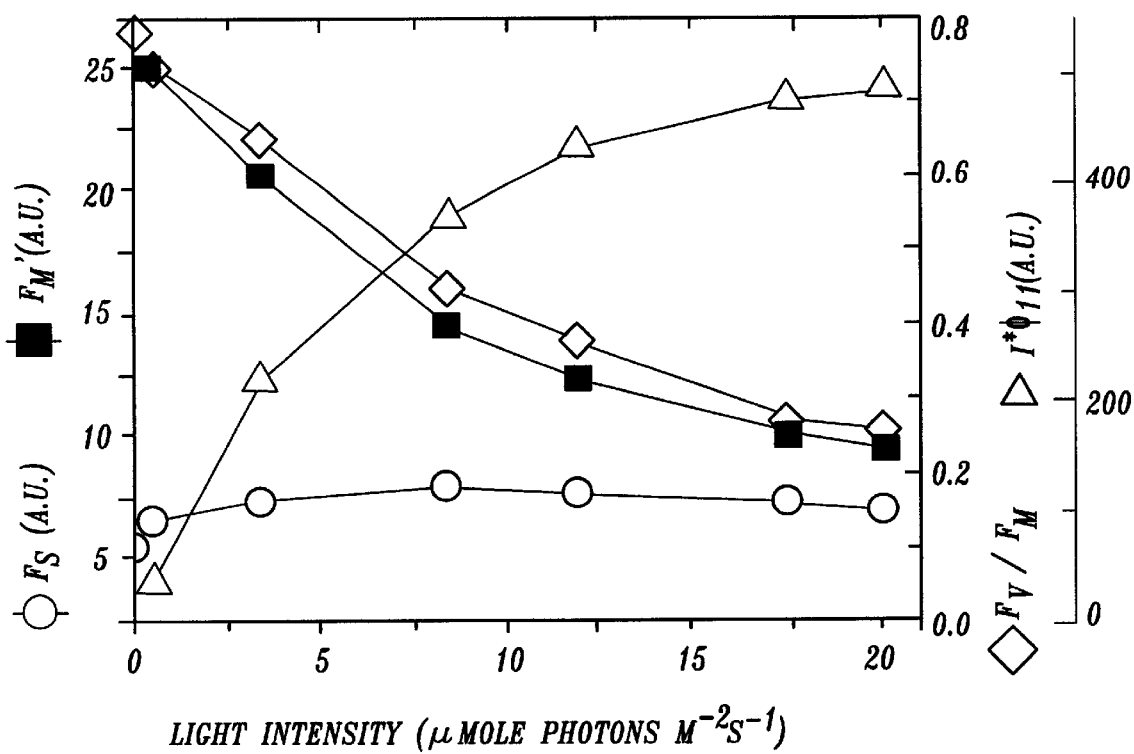
FIG. 20 shows chlorophyll a fluorescence yield parameters during steady-state photosynthesis in intact tobacco leaves. Fluorescence yields in the steady-state, $F_s$ (open circles), and during saturation pulses, $F_m'$ (closed squares), were obtained at varying light intensities using a diffused optics flash spectrophotometer as described in Example 10. The quantum yield of photosystem II and associated light harvesting complexes ($F_V/F_M'$ or $\phi_{II}$, open diamonds) and an estimate of photosystem II electron flux ($i^*\phi_{II}$) were calculated as described in Example 10.

FIG. 20 shows typical light-dependencies of fluorescence parameters investigated in the experiments reported in this example. The amplitude of $F_M{'}$ decreased steadily as light intensity increased, reflecting the progressive engagement of non-photochemical quenching mechanisms (e.g. Owens, T. G. (1996) in *Photosynthesis and the Environment*, ed. Baker, N. (Kluwer Academic Publishers, Dordrecht, The Netherlands), pp. 1–23). The steady-state fluorescence, $F_s$, rose from light intensities between 17 and 800 $\mu$mol photons $m^{-2}s^{-1}$, reflecting a net steady-state reduction of $Q_A$. It then fell between 800 and 2000 $\mu$mole photons $m^{-2}s^{-1}$, reflecting the onset of strong non-photochemical quenching (reviewed in Genty, B. & Harbinson, J. (1996) in *Photosynthesis and the Environment*, ed. Baker, N. R. (Kluwer Academic Publishers, The Netherlands), pp. 67–99; Govindjee (1995) *Aust. J. Plant Physiol.* 22, 20–29; Horton, P., Ruban, A. & Walters, R. (1996) *Annu. Rev. Plant Physiol. Plant. Mol. Biol.* 47, 655–684). Under dark-adapted conditions, the photochemical quantum efficiency of PS II and associated antenna, estimated by $\phi_{II}$, was between 0.75 and 0.81 for all leaves measured. The value of $\phi_{II}$ decreased as light intensity was increased, reaching between 0.15 to 0.22 at about 2000 $\mu$mol photons $m^{-2}s^{-1}$. The flux of electrons through PS II, as estimated by $i^*\phi_{II}$, showed a typical light saturation curve, reaching half maximal value at about 450 $\mu$mol photons $m^{-2}s^{-1}$.

Dark interval relaxation kinetics. Typical $-\Delta I/I_0$ changes that occurred during DIRK experiments are shown in FIG. 21 and were essentially as described previously. The pronounced signature of the ECS was observed between 500 and 545 nm (Witt, H. T. (1979) *Biochim. Biophys. Acta* 505, 355–427), whereas contributions from redox changes in the cyt $b_6f$ complex occurred in the 545–570 nm region, most notably an absorbance increase due to reduction of cyt f ($\alpha$-band peak at 554 nm). Moreover, the spectral changes were consistent with major contributions from ECS and cyt f over the entire time course of the decay, from 1 to 40 ms after shutter closure, indicating that the deconvolution procedures utilized herein yielded good representations of cyt f and ECS signals. Absorbance changes at 830 nm, associated with $P_{700}$ reduction, were similar to those reported earlier (e.g. Klughammer, C. & Schreiber, U. (1994) *Planta* 192, 261–268; Laisk, A. & Oja, V. (1994) *Photosynthesis Research* 39, 39–50; Klughammer, C. & Schreiber, U. (1991) *Z. Naturforsch.* 46c, 233–244; Klughammer, C. & Schreiber, U. (1998) in *Photosynthesis. Mechanisms and Effects*, ed. Garab, G. (Kluwer Academic Publishers, Dordrect), Vol. V, pp. 4357–4360). The half-times for the relaxation ranged from approximately from 10 to 6 ms for $P_{700}$ and 17 to 12 ms for cyt f as light intensity was changed from 10 to 1600 $\mu$moles·$m^{-2}$·$s^{-1}$, in line with data presented by several groups (Laisk, A. & Oja, V. (1994) *Photosynthesis Research* 39, 39–50; Harbinson, J., Genty, B. & Baker, N. R. (1989) *Plant Physiol.* 90, 1029–1034; Laisk, A. & Oja, V. (1995) *Photosynth. Res.* 45, 11–19; Ott, T., Clarke, J., Birks, K. & Johnson, G. (1999) *Planta* 209, 250–258; Kramer, D. M., Sacksteder, C. A. & Cruz, J. A. (1999) *Photosynth. Res.* 60, 151–163). The halftimes for the decay of the ECS remained in a narrow range from 18 to 20 ms over the entire range of light intensities. This implies that neither electron transfer nor ATP synthesis were hindered by product inhibition, substrate depletion, or feedback processes. The initial rates of relaxation for the electrochromic shift, i.e. $DIRK_{ECS}$, were estimated by fitting a line through the 520 nm data 2–8 ms after closure of the shutter.

Figure 23:
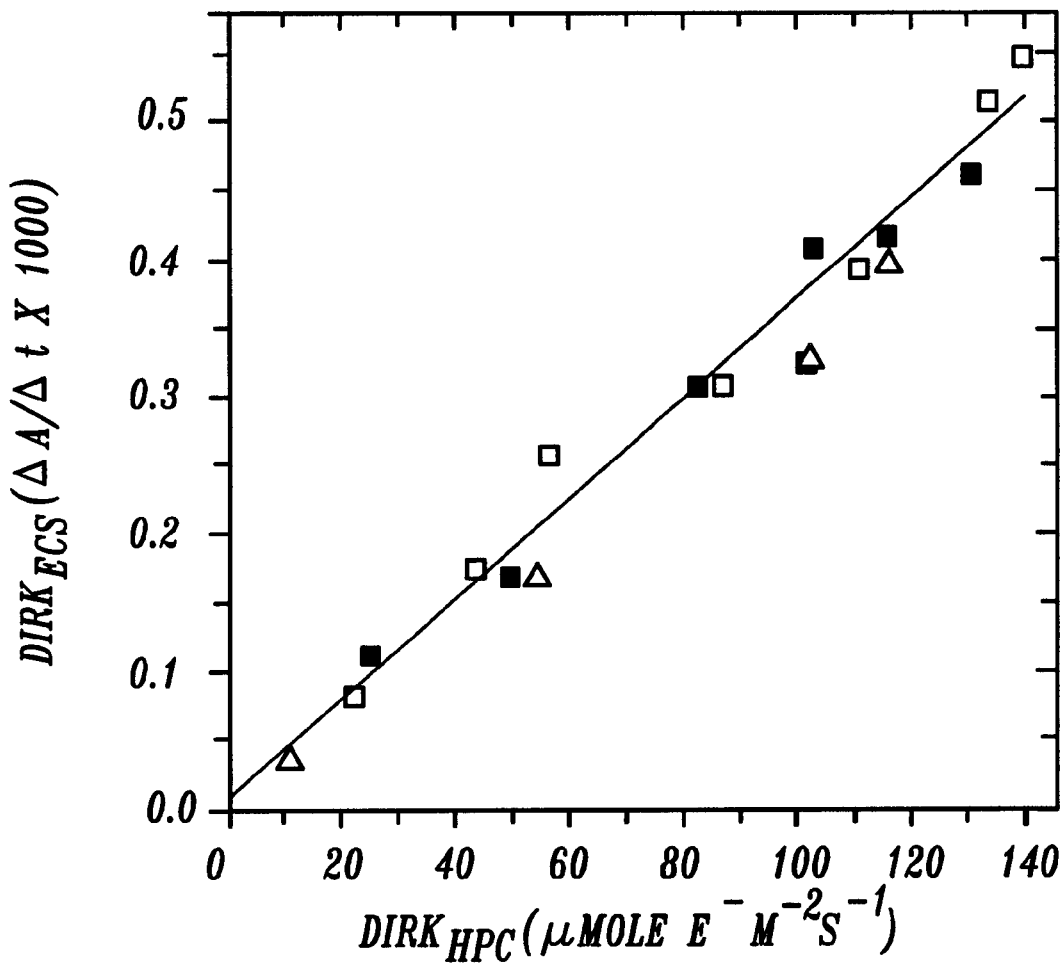
FIG. 23 shows a comparison of DIRK$_{ECS}$, estimating proton pumping, and DIRK$_{hpc}$, estimating electron flux through the cytochrome b$_6$f complex and PS I. Values were calculated as described in Example 10. The different symbols represent data taken from three separate plants. The r-value of the best-fit line was 0.992.

Within the noise level, the magnitudes of $DIRK_{ECS}$ and $DIRK_{hpc}$ initial rates were proportional to PS II electron flux as measured by $i^*\phi_{II}$, (FIGS. 22 and 23). Moreover, the relationship remained linear when the initial rate for $DIRK_{ESC}$ was taken at a wide range of time intervals, or when the full extent of ECS signal was used. This indicates that residual cyt $b_6f$ complex turnover did not impact the $DIRK_{ECS}$ signal. These relationships are further substantiated in a preliminary report (Sacksteder, C. A. & Kramer, D. M. (1998) in *Photosynthesis: Mechanisms and Effects*, ed. Garab (Kluwer Academic Publishers, Dordrect), Vol. 3, pp. 1621–1624), in which a linear relationship was found between $O_2$ evolution and $DIRK_{ECS}$ under conditions similar to those reported here. Experiments performed with longer preillumination times, as well as in the reverse light-intensity order, gave nearly identical results, indicating that induction phenomena did not significantly impact the results.

The relationships between relative fluxes of electrons transferred through PS II and protons passed through the ATPase, were found to be linear within the noise level (FIGS. 22 and 23). This indicates that $H^+/e^-$ remained constant over the entire light saturation curve. Most recent measurements agree that the $H^+/e^-$ ratio for linear electron flow is 3 at low light intensities (Berry, S. & Rumberg, B. (1999) *Biochim. Biophys. Acta* 1410, 248–261; Kramer, D. M., Sacksteder, C. A. & Cruz, J. A. (1999) *Photosynth. Res.* 60, 151–163; Kobayashi, Y., Neimanis, S. & Heber, U. (1995) *Plant Cell Physiol.* 36, 1613–1620). From the data presented herein, it is inferred that the $H^+/e^-$ ratio remains at 3 in healthy, unstressed plants.

Finally, it is worthwhile noting that the linear relationships between the DIRK techniques and the $i^*\phi_{II}$ parameter (Genty, B., Harbinson, J. & Baker, N. R. (1990) *Plant Physiol. Biochem.* 28, 1–10) as well as gas exchange (see Example 9 herein, and; Sacksteder, C. A. & Kramer, D. M. (1998) in *Photosynthesis: Mechanisms and Effects*, ed. Garab (Kluwer Academic Publishers, Dordrect), Vol. 3, pp. 1621–1624) tend to validate the use of these measurements as linear indicators of flux. The DIRK approach should be particularly useful as an independent test of fluorescence estimates under extreme conditions where the validity of the more commonly used technique has not been fully established.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for measuring a photosynthetic parameter comprising:
   (a) illuminating a plant leaf until steady-state photosynthesis is achieved;

(b) subjecting the illuminated plant leaf to a period of darkness;

(c) using a kinetic spectrophotometer or kinetic spectrophotometer/fluorimeter to collect spectral data from the plant leaf treated in accordance with steps (a) and (b); and (d) determining a value for a photosynthetic parameter from the spectral data.

2. The method of claim 1 wherein the plant leaf is subjected to darkness for a period of time from 2 milliseconds to 120 seconds.

3. The method of claim 1 wherein a kinetic spectrophotometer is used to collect spectral data from the plant leaf.

4. The method of claim 3 wherein the kinetic spectrophotometer generates a measuring light beam having a direction that is randomized before and after passing through the plant leaf.

5. The method of claim 1 wherein a kinetic spectrophotometer/fluorimeter is used to collect spectral data from the plant leaf.

6. The method of claim 1 wherein the determined photosynthetic parameter is a redox reaction of the photosystem I primary electron donor.

7. The method of claim 6 wherein the spectral data is collected from the plant leaf by a method comprising illuminating the plant leaf with a measuring beam of light having a wavelength of 703 nm.

8. The method of claim 6 wherein the spectral data is collected from the plant leaf by a method comprising illuminating the plant leaf with a measuring beam of light having a wavelength in the range of 800–850 nm.

9. The method of claim 1 wherein the determined photosynthetic parameter is a redox reaction of plastocyanin.

10. The method of claim 9 wherein the spectral data is collected from the plant leaf by a method comprising illuminating the plant leaf with a measuring beam of light having a wavelength of 600 nm.

11. The method of claim 9 wherein the spectral data is collected from the plant leaf by a method comprising illuminating the plant leaf with a measuring beam of light having a wavelength in the range of 850–925 nm.

12. The method of claim 1 wherein the determined photosynthetic parameter is a redox reaction of cytochrome f.

13. The method of claim 12 wherein the spectral data is collected from the plant leaf by a method comprising illuminating the plant leaf with a measuring beam of light having a wavelength selected from the group consisting of 435, 545, 554 and 560 nm.

14. The method of claim 1 wherein the determined photosynthetic parameter is a redox reaction of cytochrome b.

15. The method of claim 14 wherein the spectral data is collected from the plant leaf by a method comprising illuminating the plant leaf with a measuring beam of light having a wavelength selected from the group consisting of 420, 563 and 572 nm.

16. The method of claim 1 wherein the determined photosynthetic parameter is a redox reaction of the primary quinone acceptor of photosystem II.

17. The method of claim 16 wherein the spectral data is collected from the plant leaf by a method comprising illuminating the plant leaf with a measuring beam of light having a wavelength of 300 nm.

18. The method of claim 16 wherein the spectral data is collected from the plant leaf by a method comprising illuminating the plant leaf with a measuring beam of light having a wavelength selected from the group consisting of 545, 550 and 555 nm.

19. The method of claim 1 wherein the determined photosynthetic parameter is the conversion of violaxanthin to antheraxanthin and zeaxanthin in the light harvesting complexes.

20. The method of claim 19 wherein the spectral data is collected from the plant leaf by a method comprising illuminating the plant leaf with a measuring beam of light having a wavelength of 505 nm.

21. The method of claim 1 wherein the determined photosynthetic parameter is the amount of energy stored across the thylakoid membrane.

22. The method of claim 21 wherein the spectral data is collected from the plant leaf by a method comprising illuminating the plant leaf with a measuring beam of light having a wavelength selected from the group consisting of 470 and 520 nm.

23. The method of claim 1 wherein the determined photosynthetic parameter is the fraction of open photosystem II reaction centers.

24. The method of claim 23 wherein the spectral data is collected from the plant leaf by a method comprising illuminating the plant leaf with a measuring beam of light having a wavelength greater than 650 nm.

25. The method of claim 1 further comprising the step of using the determined value for the photosynthetic parameter to determine the physiological state of a plant.

26. The method of claim 25 wherein the step of using the determined value for the photosynthetic parameter to determine the physiological state of a plant comprises the step of comparing the determined value for the photosynthetic parameter to a reference value for the same photosynthetic parameter determined from spectral data obtained from one or more reference plants.

27. The method of claim 26 further comprising the step of observing a difference between the determined value for the photosynthetic parameter and the reference value for the photosynthetic parameter.

28. The method of claim 27 further comprising the step of correlating the difference between the determined value for the photosynthetic parameter and the reference value for the photosynthetic parameter with the presence of a physiological stress in the plant.

29. The method of claim 28 wherein:

(a) the photosynthetic parameter is ATP synthase activity;

(b) the determined value for ATP synthase activity is greater than the reference value for ATP synthase activity; and (c) the difference between the determined value for ATP synthase activity and the reference value for ATP synthase activity is correlated with the presence of drought stress in the plant.

30. The method of claim 28 wherein:

(a) the photosynthetic parameter is $P_{700}$ reduction;

(b) the determined value for $P_{700}$ reduction is greater than the reference value for $P_{700}$ reduction; and (c) the difference between the determined value for $P_{700}$ reduction and the reference value for $P_{700}$ reduction is correlated with the presence of drought stress in the plant.

31. The method of claim 28 wherein:

(a) the photosynthetic parameter is the proton/electron resistance ratio;

(b) the determined value for the proton/electron resistance ratio is greater than the reference value for the proton/electron resistance ratio; and (c) the difference between the determined value for the proton/electron resistance ratio and the reference value for the proton/electron resistance ratio is correlated with the presence of drought stress in the plant.

32. The method of claim 28 wherein:

(a) the photosynthetic parameter is ATP synthase activity;

(b) the determined value for ATP synthase activity is less than the reference value for ATP synthase activity; and (c) the difference between the determined value for ATP synthase activity and the reference value for ATP synthase activity is correlated with the presence of nitrogen stress in the plant.

33. The method of claim 28 wherein:

(a) the photosynthetic parameter is $P_{700}$ reduction;

(b) the determined value for $P_{700}$ reduction is less than the reference value for $P_{700}$ reduction; and (c) the difference between the determined value for $P_{700}$ reduction and the reference value for $P_{700}$ reduction is correlated with the presence of nitrogen stress in the plant.

34. The method of claim 28 wherein:

(a) the photosynthetic parameter is the proton/electron resistance ratio;

(b) the determined value for the proton/electron resistance ratio is less than the reference value for the proton/electron resistance ratio; and (c) the difference between the determined value for the proton/electron resistance ratio and the reference value for the proton/electron resistance ratio is correlated with the presence of nitrogen stress in the plant.

35. A method for determining the physiological state of a plant comprising:

(a) illuminating a plant leaf until steady-state photosynthesis is achieved;

(b) subjecting the illuminated plant leaf to a period of darkness;

(c) using a kinetic spectrophotometer or kinetic spectrophotometer/fluorimeter to collect spectral data from the plant leaf treated in accordance with steps (a) and (b);

(d) determining a value for a photosynthetic parameter from the spectral data; and (e) using the determined value for the photosynthetic parameter to determine the physiological state of the plant.

36. The method of claim 35 wherein the step of using the determined value for the photosynthetic parameter to determine the physiological state of a plant comprises the step of comparing the determined value for the photosynthetic parameter to a reference value for the same photosynthetic parameter calculated from spectral data obtained from one or more reference plants.

37. The method of claim 36 further comprising the step of observing a difference between the determined value for the photosynthetic parameter and the reference value for the photosynthetic parameter.

38. The method of claim 37 further comprising the step of correlating the difference between the determined value for the photosynthetic parameter and the reference value for the photosynthetic parameter with the presence of a physiological stress in the plant.

39. The method of claim 38 wherein:

(a) the photosynthetic parameter is ATP synthase activity;

(b) the determined value for ATP synthase activity is greater than the reference value for ATP synthase activity; and (c) the difference between the determined value for ATP synthase activity and the reference value for ATP synthase activity is correlated with the presence of drought stress in the plant.

40. The method of claim 38 wherein:

(a) the photosynthetic parameter is $P_{700}$ reduction;

(b) the determined value for $P_{700}$ reduction is greater than the reference value for $P_{700}$ reduction; and (c) the difference between the determined value for $P_{700}$ reduction and the reference value for $P_{700}$ reduction is correlated with the presence of drought stress in the plant.

41. The method of claim 38 wherein:

(a) the photosynthetic parameter is the proton/electron resistance ratio;

(b) the determined value for the proton/electron resistance ratio is greater than the reference value for the proton/electron resistance ratio; and (c) the difference between the determined value for the proton/electron resistance ratio and the reference value for the proton/electron resistance ratio is correlated with the presence of drought stress in the plant.

42. The method of claim 38 wherein:

(a) the photosynthetic parameter is ATP synthase activity;

(b) the determined value for ATP synthase activity is less than the reference value for ATP synthase activity; and (c) the difference between the determined value for ATP synthase activity and the reference value for ATP synthase activity is correlated with the presence of nitrogen stress in the plant.

43. The method of claim 38 wherein:

(a) the photosynthetic parameter is $P_{700}$ reduction;

(b) the determined value for $P_{700}$ reduction is less than the reference value for $P_{700}$ reduction; and (c) the difference between the determined value for $P_{700}$ reduction and the reference value for $P_{700}$ reduction is correlated with the presence of nitrogen stress in the plant.

44. The method of claim 38 wherein:

(a) the photosynthetic parameter is the proton/electron resistance ratio;

(b) the determined value for the proton/electron resistance ratio is less than the reference value for the proton/electron resistance ratio; and (c) the difference between the determined value for the proton/electron resistance ratio and the reference value for the proton/electron resistance ratio is correlated with the presence of nitrogen stress in the plant.

* * * * *